United States Patent [19]

Rody

[11] 4,061,631

[45] Dec. 6, 1977

[54] 1-AZA-4-THIACYCLOHEXANE-4,4-DIOXIDE DERIVATIVES

[75] Inventor: Jean Rody, Basel, Switzerland

[73] Assignee: Ciba-Geigy Corporation, Ardsley, N.Y.

[21] Appl. No.: 651,500

[22] Filed: Jan. 22, 1976

Related U.S. Application Data

[62] Division of Ser. No. 407,000, Oct. 16, 1973, Pat. No. 3,943,098.

[51] Int. Cl.$^2$ ............................................. C07D 279/12
[52] U.S. Cl. ................................ 544/53; 260/45.8 SN; 260/570.8 R; 560/44; 560/39; 560/34; 560/81
[58] Field of Search ..................................... 260/243 R

[56] References Cited

U.S. PATENT DOCUMENTS

| | | | |
|---|---|---|---|
| 3,505,320 | 4/1970 | Dabritz et al. | 260/243 |
| 3,770,732 | 11/1973 | Quinlan | 260/243 |
| 3,903,082 | 9/1975 | Berger | 260/243 |

*Primary Examiner*—John M. Ford
*Attorney, Agent, or Firm*—Nestor W. Shust

[57] ABSTRACT

New 1-aza-4-thiacyclohexane-4,4-dioxide derivatives are used alone or in combination with other stabilizers for stabilizing organic materials. The new compounds are prepared by reacting substituted diallylsulfides with ammonia, amines or hydrazines.

15 Claims, No Drawings

1-AZA-4-THIACYCLOHEXANE-4,4-DIOXIDE DERIVATIVES

This is a division of application Ser. No. 407,000 filed Oct. 16, 1973, now U.S. Pat. No. 3,943,098.

The invention relates to new 1-aza-4-thiacylcohexane-4,4-dioxide derivatives and to stabiliser systems containing these new compounds, to their use for the protection of organic material, as well as to the material, as an industrial product, protected with the aid of the new compounds.

The invention concerns new compounds of formula I

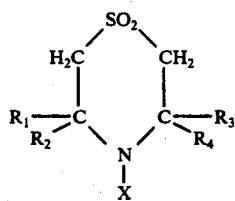

wherein
$R_1$, $R_2$, $R_3$ and $R_4$ each independently represent lower alkyl, or $R_1$ and $R_2$ and/or $R_3$ and $R_4$ together with the carbon atom to which they are bound form a cycloalkyl ring, and X represents hydrogen, unsubstituted alkyl, substituted alkyl, alkenyl, alkynyl, unsubstituted aralkyl, substituted aralkyl, acyl, halogen, —O., —NO or $NR_5R_6$ wherein $R_5$ and $R_6$ each independently represent hydrogen, unsubstituted alkyl or substituted alkyl, or $R_5$ is additionally acyl, or $R_5$ and $R_6$ together with the nitrogen atom to which they are bound form a ring, or their salts with organic or inorganic acids.

Preferred compounds of formula I are those wherein $R_1$, $R_2$, $R_3$ and $R_4$ represent alkyl having 1 to 4 carbon atoms, or $R_1$ and $R_2$ as well as $R_3$ and $R_4$ together with the carbon atom to which they are bound form a cyclopentane or cyclohexane ring, and X represents hydrogen, unsubstituted alkyl having 1 to 18 carbon atoms, alkyl having 2 to 20 carbon atoms which is substituted with groups containing O, N or S, alkenyl having 3 to 18 carbon atoms, alkynyl having 3 to 14 carbon atoms, unsubstituted aralkyl having 7 to 11 carbon atoms, aralkyl having 9 to 18 carbon atoms which is substituted by hydroxy, ester groups or halogen, acyl of the formulae $R_7CO—$ or $R_7SO_2—$ wherein $R_7$ represents alkyl having 1 to 18 carbon atoms, aryl having 6 to 10 carbon atoms or aralkyl having 7 to 11 carbon atoms, halogen, —O., —NO or —$NR_5R_6$ wherein $R_5$ and $R_6$ each independently represent hydrogen, unsubstituted alkyl having 1 to 12 carbon atoms, alkyl having 2 to 12 carbon atoms which is substituted with groups containing O, N or S, or $R_5$ is additionally $R_7CO—$ or $R_7SO_2$, or together with the nitrogen atom to which they are bound they form a ring, or their salts with hydrohalic acids, sulphuric acid, carboxylic acids, sulphonic acids or phosphorus-containing acids.

Particularly preferred compounds of formula I are those wherein
$R_1$, $R_2$, $R_3$ and $R_4$ represent alkyl having 1 or 2 carbon atoms, or $R_1$ and $R_2$ as well as $R_3$ and $R_4$ together with the carbon atom to which they are bound form a cyclohexane ring, and X represents hydrogen, unsubstituted alkyl having 1 to 12 carbon atoms, alkyl having 2 to 20 carbon atoms which is substituted with hydroxy, carboxy, ester, amide, nitrile, ether, thioether, sulphoxide, sulphone or amino groups, alkenyl having 3 to 8 carbon atoms, propargyl, aralkyl having 7 to 11 carbon atoms, aralkyl having 9 to 18 carbon atoms which is substituted by hydroxy, carboxylic acid ester groups or halogen, acyl of the formulae $R_7CO—$ or $R_7SO_2—$ wherein $R_7$ is alkyl having 1 to 12 carbon atoms, aryl having 6 to 10 carbon atoms or aralkyl having 7 to 11 carbon atoms, bromine, chlorine, —O. or —$NR_5R_6$ wherein $R_5$ and $R_6$ each independently represent hydrogen, alkyl having 1 to 4 carbon atoms, or $R_5$ is additionally $R_7CO—$ or $R_7SO_2—$, or their salts with hydrohalic acids, sulphuric acid, phosphoric acid, carboxylic acids having 1 to 18 carbon atoms, sulphonic acids having 1 to 12 carbon atoms, or phosphorus-organic acids having 1 to 20 carbon atoms.

A special group among the particularly preferred compounds of formula I is formed by compounds of formula Ia

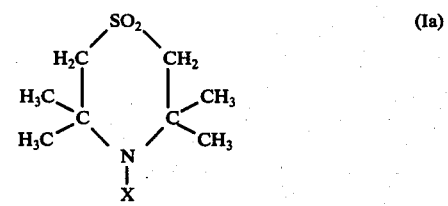

wherein
X represents hydrogen, alkyl having 1 to 12 carbon atoms, cyanomethyl, alkenyl having 3 to 8, preferably 3 or 4, carbon atoms, propargyl, aralkyl having 7 to 11 carbon atoms, chlorine, bromine, —O., —NO or —$NR_5R_6$ wherein $R_5$ and $R_6$ each independently represent hydrogen, alkyl having 1 to 4 carbon atoms, or $R_5$ is additionally alkylcarbonyl having 2 to 12 carbon atoms, alkoxycarbonyl having 2 to 8 carbon atoms or, preferably, ethoxycarbonyl or benzoyl, or their salts with carboxylic acids having 1 to 18 carbon atoms, preferably 3,5-ditert.butyl-4-hydroxybenzoic acid, or phosphorus-organic acids having 1 to 20 carbon atoms.

Surprisingly, it has been found that the compounds of formula I are good stabilisers for organic substrates such as polymers, especially synthetic polymers, against light-induced degradation.

1-Aza-4-thiacyclohexane-4,4-dioxide derivatives are already known. They exhibit no protective action against th effect of light. Surprisingly, the new compounds of formula I are agents protecting against light rays in the case of organic substrates such as polymers.

$R_1$, $R_2$, $R_3$ and $R_4$ can be, as defined, lower alkyl groups. They can be methyl, ethyl, n-propyl, iso-propyl, n-butyl, sec.butyl, tert.butyl, n-amyl, tert.amyl or n-hexyl. X, $R_5$ and/or $R_6$ can be alkyl groups; these can be the same groups as in the case of $R_1$ to $R_4$, and additionally n-octyl, n-decyl, n-dodecyl, n-tetradecyl, n-hexadecyl or n-octadecyl. If $R_1$ and $R_2$ and/or $R_3$ and $R_4$ in formula I denote cycloalkyl, then they can be cyclopentyl, cyclohexyl or cyclooctyl. Examples for substituted alkyl denoted by X, $R_5$ and/or $R_6$ are: hydroxyalkyl such as $-CH_2CH_2OH$ or $-CH_2-CHOH-CH_3$; carboxyalkyl such as $-CH_2-COOH$; alkyl substituted with ester groups such as, e.g. carboxylic acid ester groups, for example, alkoxycarbonylalkyl such as $-CH_2COOCH_3$, $-CH_2COOC_2H_5$, $-CH_2COOC_8H_{17}$, $-CH_2COOC_{12}H_{25}$ or $-CH_2COOC_{18}H_{37}$, for example, alkylcarbonyloxyalkyl such as $-CH_2CH_2OOCCH_3$, $-CH_2CH_2OOCC_7H_{15}$, $-CH_2CH_2OOCC_{11}H_{23}$, $-CH_2CH_2OOCC_{17}H_{35}$ or

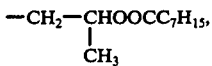

for example, arylcarbonyloxyalkyl, preferably benzoyloxyalkyl, such as

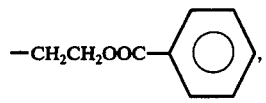

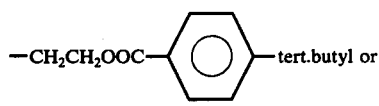

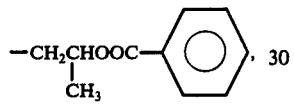

for example, cycloalkylcarbonyloxyalkyl such as

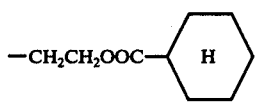

or, for example, aralkylcarbonyloxyalkyl, preferably benzylcarbonyloxyalkyl such as

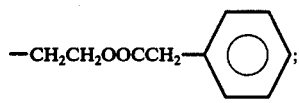

amidoalkyl such as alkylcarbonylamidoalkyl, for example, $-CH_2CH_2NH-CO-C_7H_{15}$, $-CH_2CH_2CH_2NH-CO-CH_3$ or $-CH_2CH_2CH_2NH-CO-C_{17}H_{35}$; nitriloalkyl, for example, $-CH_2CN$ or $-CH_2CH_2CN$; alkyl substituted with ether groups such as alkoxy groups, for example, $-CH_2CH_2OC_8H_{17}$; alkyl substituted with thioether groups such as alkylthio groups, for example, $-CH_2CH_2SC_8H_{17}$, or alkyl substituted with arylthio groups, preferably phenylthio groups, for example,

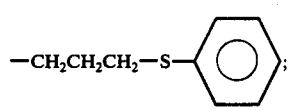

alkyl substituted with sulphoxide groups, such as alkylsulphinylalkyl, for example, $-CH_2CH_2SO\ C_8H_{17}$; alkyl substituted with sulphone groups, such as alkylsulphonylalkyl, for example, $-CH_2CH_2CH_2C_{12}H_{25}$; aminoalkyl such as aminoalkyl unsubstituted on the nitrogen atom, for example, $-CH_2CH_2NH_2$ or $-CH_2CH_2CH_2NH_2$, or such as aminoalkyl substituted on the nitrogen atom with alkyl, for example, $-CH_2CH_2-N(CH_3)_2$, $-CH_2CH_2CH_2N(C_2H_5)_2$ or $-CH_2CH_2NHCH_2CH_2CN$; haloalkyl, preferably chloro- or bromoalkyl, for example, $-CH_2CH_2Cl$, $-CH_2CH_2Br$ or

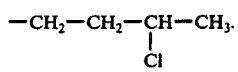

$R_5$ and $R_6$ together with the nitrogen atom to which they are bound can form a ring, such as, for example, the piperidine or morpholine ring.

If X denotes alkenyl, then it can be propenyl, butenyl, pentenyl, hexenyl, octenyl, decenyl, tetracenyl or octadecenyl. If X represents alkynyl, then it can be, for example, propargyl. Where X denotes unsubstituted aralkyl, it can be benzyl, α-phenylethyl or α,α-dimethylbenzyl. If X stands for a substituted aralkyl, then it can be an aralkyl substituted on the alkylene moiety by hydroxy, for example,

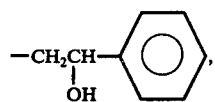

by alkylcarbonyloxy, for example,

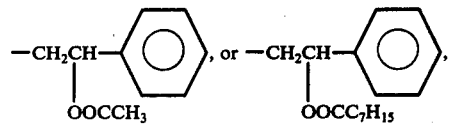

by arylcarbonyloxy, preferably phenylcarbonyloxy, for example

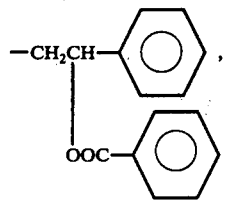

or by halogen, preferably chlorine or bromine, for example,

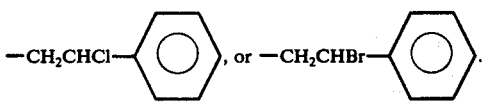

If X and/or $R_5$ represent acyl, then it is, for example, the radical of an aliphatic or aromatic carboxylic acid having 2 to 18 carbon atoms, such as alkanoic acid such as acetic acid, propionic acid, capronic acid, lauric acid or stearic acid, or an unsubstituted or substituted benzoic acid, such as benzoic acid, p-tert. butylbenzoic acid or p-tert.octylbenzoic acid, or the radical of a sulphonic acid such as methanesulphonic acid, benzenesulphonic acid or p-toluenesulphonic acid. Where X represents halogen, it can be chlorine or bromine.

The compounds of formula I are in the form of free bases, or in the form of salts of organic acids, such as, for example, an alkanoic acid preferably having 2 to 18 carbon atoms, such as acetic acid, caproic acid, lauric acid or stearic acid, or of an unsubstituted or substituted benzoic acid, such as benzoic acid or 3,5-di-tert.-butyl-4-hydroxybenzoic acid; or salts of inorganic acids such as, for example, hydrochloric acid, hydrobromic acid, sulphuric acid or phosphoric acid.

Examples of compounds of formula I are:

2,6-dimethyl-2,6-diethyl-1-aza-4-thiacyclohexane-4,4-dioxide,
2,2,6,6-tetramethyl-1-aza-4-thiacyclohexane-4,4-dioxide,
2,2-dimethyl-6,6-pentylene-1-aza-4-thiacyclohexane-4,4-dioxide,
1,2,2,6-tetramethyl-6-isopropyl-1-aza-4-thiacyclohexane-4,4-dioxide,
2,2-pentylene-6,6-pentylene-1-aza-4-thiacyclohexane-4,4-dioxide,
2,2,6-trimethyl-6-n-butyl-1-aza-4-thiacyclohexane-4,4-dioxide,
1,2,2,6,6-pentamethyl-1-aza-4-thiacyclohexane-4,4-dioxide,
1-n-propyl-2,2,6,6-tetramethyl-1-aza-4-thiacyclohexane-4,4-dioxide,
1-iso-butyl-2,2,6,6-tetramethyl-1-aza-4-thiacyclohexane-4,4-dioxide,
1-carbethoxymethyl-2,2,6,6-tetramethyl-1-aza-4-thiacyclohexane-4,4-dioxide,
1-(2'-hydroxyethyl)-2,2,6,6-tetramethyl-1-aza-4-thiacyclohexane-4,4-dioxide,
1-(2'-phenyl-2'-hydroxyethyl)-2,2,6,6-tetramethyl-1-aza-4-thiacyclohexane-4,4-dioxide,
1-acetoxyethyl-2,2,6,6-tetramethyl-1-aza-4-thiacyclohexane-4,4-dioxide,
1-(2'-phenyl-2'-acetoxyethyl)-2,2,6,6-tetramethyl-1-aza-4-thiacyclohexane-4,4-dioxide,
1-octylamino-2,2,6,6-tetramethyl-1-aza-4-thiacyclohexane-4,4-dioxide,
1-dimethylamino-2,2,6,6-tetramethyl-1-aza-4-thiacyclohexane-4,4-dioxide,
1-diethylamino-2,2,6,6-tetramethyl-1-aza-4-thiacyclohexane-4,4-dioxide,
1-acetyl-methylamino-2,2,6,6-tetramethyl-1-aza-thiacyclohexane-4,4-dioxide,
1-acetylamino-2,2,6,6-tetramethyl-1-aza-4-thiacyclohexane-4,4-dioxide,
1-octanoylamino-2,2,6,6-tetramethyl-1-aza-4-thiacyclohexane-4,4-dioxide,
1-lauroylamino-2,2,6,6-tetramethyl-1-aza-4-thiacyclohexane-4,4-dioxide,
1-ethoxycarbonylamino-2,2,6,6-tetramethyl-1-aza-4-thiacyclohexane-4,4-dioxide,
1-acetyl-2,2,6,6-tetramethyl-1-aza-4-thiacyclohexane-4,4-dioxide,
1-lauroyl-2,2,6,6-tetramethyl-1-aza-thiacyclohexane-4,4-dioxide,
1-benzoyl-2,2,6,6-tetramethyl-1-aza-4-thiacyclohexane-4,4-dioxide,
1-(4'-butylbenzoyl)-2,2,6,6-tetramethyl-1-aza-4-thiacyclohexane-4,4-dioxide,
1-methylsulphonyl-2,2,6,6-tetramethyl-1-aza-4-thiacyclohexane-4,4-dioxide,
1-p-toluylsulphonyl-2,2,6,6-tetramethyl-1-aza-4-thiacyclohexane-4,4-dioxide,
1-phenylacetyl-2,2,6,6-tetramethyl-1-aza-4-thiacyclohexane-4,4-dioxide,
1-p-t.butylphenylacetyl-2,2,6,6-tetramethyl-1-aza-4-thiacyclohexane-4,4-dioxide,
1-octadecyl-2,2,6,6-tetramethyl-1-aza-4-thiacyclohexane-4,4-dioxide,
1-benzyl-2,2,6,6-tetramethyl-1-aza-4-thiacyclohexane-4,4-dioxide,
1-ethoxycarbonylamino-2,2,6,6-tetramethyl-1-aza-4-thiacyclohexane-4,4-dioxide,
1-p-t.butylbenzyl-2,2,6,6-tetramethyl-1-aza-4-thiacyclohexane-4,4-dioxide,
1-dibutylamino-2,2,6,6-tetramethyl-1-aza-4-thiacyclohexane-4,4-dioxide,
1-octoxycarbonylamino-2,2,6,6-tetramethyl-1-aza-4-thiacyclohexane-4,4-dioxide,
1-carbo-octadecyloxymethyl-2,2,6,6-tetramethyl-1-aza-4-thiacyclohexane-4,4-dioxide,
1-(2'-carboxyethyl)-2,2,6,6-tetramethyl-1-aza-4-thiacyclohexane-4,4-dioxide,
1-(3'-dimethylaminopropyl)-2,2,6,6-tetramethyl-1-aza-4-thiacyclohexane-4,4-dioxide,
1-(2'-octoxyethyl)-2,2,6,6-tetramethyl-1-aza-4-thiacyclohexane-4,4-dioxide,
1-(3'-dodecylmercaptopropyl)-2,2,6,6-tetramethyl-1-aza-4-thiacyclohexane-4,4-dioxide, and
1-methallyl-2,2,6,6-tetramethyl-1-aza-4-thiacyclohexane-4,4-dioxide.

The new compounds of formula 1 are used as stabilisers for organic substrates. The following, for example, are suitable as such:

1. Polymers which are derived from hydrocarbons with single or double unsaturation, such as polyolefins, such as, for example, polyethylene, which can optionally be crosslinked, polypropylene, polyisobutylene, polymethylbutene-1, polymethylpentene-1, polybutene-1, polyisoprene, polybutadiene, polystyrene, polyisobutylene, copolymers of the monomers on which the homopolymers mentioned are based, such as ethylene-propylene copolymers, propylenebutene-1 copolymers, propylene-isobutylene copolymers, styrene-butadiene copolymers and terpolymers of ethylene and propylene with a diene, such as, for example, hexadiene, dicyclopentadiene or ethylidene-norbornene; mixtures of the abovementioned homopolymers, such as, for example, mixtures of polypropylene and polyethylene, polypropylene and polybutene-1, or polypropylene and polyisobutylene.

2. Vinyl polymers containing halogen, such as polyvinyl chloride, polyvinylidene chloride, polyvinyl fluoride, polychloroprene and chlorinated rubbers.

3. Polymers which are derived from α,β-unsaturated acids and their derivatives, such as polyacrylates and polymethacrylates, polyacrylamides and polyacrylonitrile, as well as their copolymers with other vinyl compounds, such as acrylonitrile/butadiene/styrene, acrylonitrile/styrene and acrylonitrile/styrene/acrylic ester copolyers.

4. Polymers which are derived from unsaturated alcohols and amines or their acyl derivatives or acetals, such as polyvinyl alcohol, polyvinyl acetate, polyvinyl stearate, polyvinyl benzoate, polyvinyl maleate, polyvinyl butyral, polyallyl phthalate, polyallyl melamine and their copolymers with other vinyl compounds, such as ethylene/vinyl acetate copolymers.

5. Homopolymers and copolymers which are derived from epoxides, such as polyethylene oxide or the polymers which are derived from bis-glycidyl ethers.

6. Polyacetals, such as polyoxymethylene and polyoxyethylene, as well as those polyoxymethylenes which contain ethylene oxide as the comonomer.

7. Polyphenylene oxides,

8. Polyurethanes and polyureas,

9. Polycarbonates,

10. Polysulphones,

11. Polyamides and copolyamides which are derived from diamines and dicarboxylic acids and/or from aminocarboxylic acids or the corresponding lactams, such as polyamide 6, polyamide 6/6, polyamide 6/10, polyamide 11 and polyamide 12.

12. Polyesters which are derived from dicarboxylic acids and dialcohols and/or from hydroxycarboxylic acids or the corresponding lactones, such as polyethylene glycol terephthalate or poly-1,4-dimethylolcyclohexane terephthalate, as well as their starting materials, such as lower terepthalic acid alkyl esters.

13. Crosslinked polymers which are derived from aldehydes on the one hand and phenols, ureas and melamines on the other, such as phenol-formaldehyde, urea-formaldehyde and melamine-formaldehyde resins.

14. Alkyd resins, such as glycerine-phthalic acid resins and their mixtures with melamine-formaldehyde resins.

15. Unsaturated polyester resins which are derived from copolyesters of saturated and unsaturated dicarboxylic acids with polyhydric alcohols, with vinyl compounds as crosslinking agents, and also their halogen-containing, difficultly combustible modifications.

16. Natural polymers such as cellulose and rubber, as well as their polymer-homologously chemically modified derivatives, such as cellulose acetates, cellulose propionates and cellulose butyrates, or the cellulose ethers, such as methylcellulose.

Preferred synthetic polymers are polyethylene of high and low density, polypropylene, polybutadiene, polystyrene and their copolymers, such as acrylonitrile/butadiene/styrene, acrylonitrile/styrene or acrylonitrile/styrene/acrylic ester, as well as polyurethanes.

Besides these polymers, further suitable carriers are natural as well as synthetic light-sensitive waxes, fats and oils, and also complex systems, such as photographic material, emulsions containing light-sensitive substances, and emulsions or dispersions of the aforementioned polymers.

The new compounds are incorporated in the substrates in a concentration of 0.01 to 5 percent by weight, calculated on the material to be stabilised. The amount to be incorporated is preferably 0.05 to 1.5, and more especially 0.1 to 0.8, percent by weight of the compounds, relative to the material being stabilised.

This incorporation in the case of polymers can be effected after polymerisation, e.g. by the mixing of the compounds and optionally further additives into the melt, by the methods usually applied in practice, before or during moulding, or also by application of the dissolved or dispersed compounds to the polymers, optionally with subsequent removal of the solvent by evaporation.

The new compounds can be incorporated into the substrates to be stabilised also in the form of a master batch which contains these compounds in a concentration, for example, of 2.5 to 25 percent by weight.

In the case of crosslinked polyethylene, the compounds are added before crosslinking.

The following are to be mentioned as further additives together with which the stabilisers usable according to the invention can be employed:

1. Antioxidants 1.1. Simple 2,6-dialkylphenols such as, for example, 2,6-ditert.butyl-4-methylphenol, 2-tert.butyl-4,6-dimethylphenol, 2,6-ditert.butyl-4-methoxymethylphenol and 2,6-dioctadecyl-4-methylphenol.

1.2. Derivatives of alkylated hydroquinones such as, for example, 2,5-ditert.butyl-hydroquinone, 2,5-ditert.amyl-hydroquinone, 2,6-ditert.butyl-hydroquinone,-2,5-ditert.butyl-4-hydroxy-anisole, 3,5-ditert.butyl-4-hydroxy-anisole, tris-(3,5-ditert.butyl-4-hydroxyphenyl)-phosphite, 3,5-ditert.butyl-4-hydroxyphenyl-stearate and bis-(3,5-ditert.butyl-4-hydroxyphenyl)-adipate.

1.3. Hydroxylated thiodiphenyl ethers such as, for example, 2,2'-thiobis-(6-tert.butyl-4-methylphenol), 2,2'-thiobis-(4-octylphenol), 4,4'-thiobis-(6-tert.butyl-3-methylphenol), 4,4'-thiobis-(3,6-di-sec.amylphenol), 4,4'-thiobis-(6-tert.butyl-2-methylphenol) and 4,4'-bis(2,6-dimethyl-4-hydroxphenyl)-disulphide.

1.4. Alkylidene-bisphenols such as, for example, 2,2'-methylene-bis-(6-tert.butyl-4-methylphenol), 2,2'-methylene-bis-(6-tert.butyl-4-ethylphenol), 4,4'-methylene-bis-(6-tert.butyl-2-methylphenol), 4,4'-methylene-bis-(2,6-ditert.butylphenol), 2,6-di-(3-tert.butyl-5-methyl-2-hydroxybenzyl)-4-methylphenol, 2,2'-methylene-bis-[4-methyl-6-(α-methylcyclohexyl)-phenol], 1,1-bis-(3,5-dimethyl-2-hydroxphenyl)-butane, 1,1-bis-(5-tert.butyl-4-hydroxy-2-methylphenyl)-butane, 2,2-bis-(5-tert.butyl-4-hydroxy-2-methylphenyl)-butane, 2,2bis-(3,5-di-tert.butyl-4-hydroxphenyl)-propane, 1,1,3-tris-(5-tert.butyl-4-hydroxy-2-methylphenyl)-butane, 2,2-bis-(5-tert.butyl-4-hydroxy-2-methylphenyl)-4-n-dodecylmercapto-butane, 1,1,5,5-tetra-(5-tert.butyl-4-hydroxy-2-methylphenyl)-pentane and ethylene-glycol-bis-[3,3-bis-(3'-tert.butyl-4'-hydroxyphenyl)-butyrate].

1.5. O-, N- and S-benzyl compounds such as, for example, 3,5,3',5'-tetra-tert.butyl-4,4'-dihydroxydibenzyl ether, 4-hydroxy-3,5-dimethylbenzyl-mercaptoacetic acid octadecyl ester, tri-(3,5-di-tert.butyl-4-hydroxyphenyl)-amine and bis-(4-tert.butyl-3-hydroxy-2,6-dimethylbenzyl)-dithiol terephthalate.

1.6. Hydroxybenzylated malonic esters such as, for example, 2,2-bis-(3,5-di-tert.-butyl-2-hydroxbenzyl)-malonic acid dioctadecyl ester, 2-(3-tert.butyl-4-hydroxy-5-methylbenzyl)-malonic acid dioctadecyl ester, 2,2-bis-(3,5-ditert.butyl-4-hydroxybenzyl)-malonic acid didodecylmercapto ethylester and 2,2-bis-(3,5-ditert.butyl-4-hydroxbenzyl)-malonic acid di-[4-(1,1,3,3-tetramethylbutyl)-phenyl]-ester:

1.7. Hydroxybenzyl-aromatics such as, for example, 1,3,5-tri-(3,5-ditert.butyl-4-hydroxybenzyl)-2,4,6-trimethylbenzene, 1,4-di-(3,5-ditert.butyl-4-hydroxybenzyl)-2,3,5,6-tetramethylbenzene and 2,4,6-tri-(3,5-ditert.butyl-4-hydroxybenzyl)-phenol.

1.8. s-Triazine compounds such as, for example, 2,4-bis-octylmercapto-6-(3,5-ditert.butyl-4-hydroxyanilino)-s-triazine, 2-octylmercapto-4,6-bis-(3,5-ditert.butyl-4-hydroxyanilino)-s-triazine, 2-octylmercapto-4,6-bis-(3,5-ditert.butyl-4-hydroxyphenoxy)-s-triazine, 2,4,6-tris-(3,5-ditert.butyl-4-hydroxyphenyoxy)-s-triazine, 2,4,6-tris-(3,5-ditert.butyl-4-hydroxyphenylethyl)-s-triazine and 1,3,5-tris-(3,5-ditert.butyl-4-hydroxphenyl)-isocyanurate.

1.9. Amides of β-3,5-ditert.butyl-4-hydroxyphenyl-propionic acid such as, for example, 1,3,5-tris-(3,5-ditert. butyl-4-hydroxphenyl-propionyl)-hexahydro-s-triazine and N,N'-di-(3,5-ditert.butyl-4-hydroxphenyl-propionyl)hexamethylenediamine.

1.10. Esters of β-3,5-ditert.butyl-4-hydroxyphenyl-prionic acid with monohydric or polyhydric alcohols, such as, for example, methanol, ethanol, octadodecanol; 1,6-hexanediol; 1,9-nonanediol, ethylene glycol; 1,2-propanediol, diethylene glycol, thiodiethylene glycol, neopentyl glycol, 3-thiaundecanol, 3-thiapentadecanol, trimethylhexanediol, trimethylolethane, trimethylolpropane, pentacrythritol, tris-hydroxyethyl-isocyanaurate and 4-hydroxymethyl-1-phospha-2,6,7-trioxabicyclo[2,2,2]octane.

1.11. Esters of β-5-tert.butyl-4-hydroxy-3-methylphenylpropionic acid with monohydric or polyhydric alcohols such as, for example, methanol, ethanol, octadecanol; 1,6-hexanediol; 1,9-nonanediol, ethylene glycol; 1,2-propanediol, diethylene glycol, thiodiethylene glycol, neopentyl glycol, 3-thiaundecanol, 3-thia-pentadecanol, trimethylhexanediol, trimethylolethane, trimethylolpropane, pentaerythritol, trishydroxyethylisocyanaurate and 4-hydroxmethyl-1-phospha-2,6,7-trioxa-bicyclo[2,2,2]octane.

1.12. Esters of 3.5-diteret.butyl-4-hydroxyphenylacetic acid with monohydric or polyhydric alcohols such as, for example, methanol, ethanol, octadecanol; 1,6-hexanediol; 1,9-nonanediol, ethylene glycol, 1,2-propanediol, diethylene glycol, thiodiethylene glycol, neopentyl glycol, 3-thriaundecanol, 3-thia-penadecanol, trimethylhexanediol, trimethylolethane, trimethylolpropane, pentaerythritol, trishydroxyethylisocyanurate and 4-hydroxymethyl-1-phospha-2,6,7-trioxabicyclo[2,2,2]octane.

1.13. Acylaminophenols such as, for example, N-(3,5-ditert.butyl-4-hydroxphenyl)-stearic acid amide and N,N'-di-(3,5-ditert.butyl-4-hydroxyphenyl)-thiobisacetamide.

1.14. Benzylphosphonates such as, for example, 3,5-ditert.butyl-4-hydroxybenzyl-phosphonic acid dimethyl ester, 3,5-ditert.butyl-4-hydroxybenzyl-phosphonic acid diethyl ester, 3,5-ditert.butyl-4-hydroxybenzyl-phosphonic acid dioctadecyl ester and 5-tert.butyl-4-hydroxy-3-methylbenzyl-phosphonic acid dioctadecyl ester.

1.15 Aminoaryl derivatives such as, for example, phenyl-1-naphthylamine, phenyl-2-naphthylamine, N,N'-diphenyl-p-phenylenediamine, N,N'-di-2-naphthyl-p-phenylenediamine, N,N'-di-2-naphthyl-p-phenylenediamine, N,N'-di-sec. butyl-p-phenylenediamine, 6-ethoxy-2,2,4-trimethyl-1,2-dihydroquinoline, 6-dodecyl-2,2,4-trimethyl-1,2-dihydroquinoline, mono- and dioctyliminobenzyl and polymerised 2,2,4-trimethyl-1,2-dihydroquinoline.

2. UV-Absorbers and agents protecting against light rays 2.1. 2-(2'-hydroxyphenyl)-benzotriazoles such as, for example, 5'-methyl, 3',5'-ditert.butyl, 5'-tert.butyl, 5'-(1,1,3,3-tetramethylbutyl), 5-chloro-3',5'-ditert.butyl, 5-chloro-3'-tert.butyl-5'-methyl, 3'-sec.butyl-5'-tert.butyl, 3'-α-methylbenzyl-5'-methyl, 3'-α-methylbenzyl-5'-methyl-5-chloro, 4'-hydroxy, 4'-methoxy, 4'-octoxy, 3',5'-ditert.amyl, 3'-methyl-5'-carbomethoxyethyl and 5-chloro-3',5'-ditert.amyl derivatives.

2.2. 2,4-bis-(2'-hydroxyphenyl)-6-alkyl-s-triazines such as, for example, 6-ethyl, 6-heptadecyl and 6-undecyl derivatives.

2.3. 2-Hydroxybenzophenones such as, for example, 4-hydroxy, 4-methoxy, 4-octoxy, 4-decyloxy, 4-dodecyloxy, 4-benzyloxy, 4,2',4'-trihydroxy and 2'-hydroxy-4,4'-dimethoxy derivatives.

2.4. 1,3-bis-(2'-hydroxybenzoyl)-benzenes such as, for example, 1,3-bis-(2'-hydroxy-4'-hexyloxy-benzoyl)-benzene, 1,3-bis-(2'-hydroxy-4'-octyloxyl-benzoyl)-benzene and 1,3-bis-(2'-hydroxy-4'-dodecyloxy-benzoyl)-benzene.

2.5. Esters, preferably aryl esters, of optionally substituted benzoic acids such as, for example, phenylsalicylate, octylphenylsalicylate, dibenzoylresorcinol, bis-(4-tert.butylbenzoyl)-resorcinol, benzoylresorcinol, 3,5-ditert.butyl-4-hydroxybenzoic acid-2,4-ditert.butylphenyl ester or -octadecyl ester or -2-methyl-4,6-ditert.butylphenyl ester.

2.6. Acrylates such as, for example, α-cyano-β,β-diphenylacrylic acid ethyl ester or -isooctyl ester, α-carbomethoxy-cinnamic acid methyl ester, α-cyano-β-methyl-p-methoxy-cinnamic acid methyl ester or -butyl ester and N-(β-carbomethoxyvinyl)-2-methyl-indoline.

2.7. Nickel compounds such as, for example, nickel complexes of 2,2'-thio-bis-[4-(1,1,3,3-tetramethylbutyl)-phenyl], such as the 1:1- or 1:2-complex, optionally with additional ligands such as n-butylamine, triethanolamine or N-cyclohexyl-di-ethanolamine, nickel complexes of bis-[2-hydroxy-4-(1,1,3,3-tetramethylbutyl)-phenyl]-sulphone, such as the 2:1-complex, optionally with additional ligands such as 2-ethylcapronic acid, nickeldibutyldithiocarbamate, nickel salts of 4-hydroxy-3,5-ditert.butylbenzyl-phosphonic acid-monoalkyl esters, such as of methyl, ethyl or butyl ester, nickel complexes of ketoximes, such as of 2-hydroxy-4-methylphenylundecylketonoxime, nickel-3,5-ditert.butyl-4-hydroxybenzoate.

2.8. Sterically hindered amines such as, for example, 4-benzoyloxy-2,2,6,6-tetramethylpiperidine, 4-stearoyloxy-2,2,6,6-tetramethylpiperidine, bis-(2,2,6,6-tetramethylpiperidyl)-sebacate, 3-n-octyl-7,7,9,9-tetramethyl-1,3,8-triaza-spiro[4,5]decane-2,4-dione.

2.9. Oxalic acid diamides such as, for example, 4,4'-dioctyloxy-oxanilide, 2,2'-di-octyloxy-5,5'-ditert.butyloxanilide, 2,2'-di-dodecyloxy-5,5'-ditert.butyloxanilide, 2-ethoxy-2'-ethyl-oxanilide, N,N'-bis-(3-dimethylaminopropyl)-oxanilide, 2-ethoxy-5-tert.butyl-2'-ethyloxanilide and their mixtures with 2-ethoxy-2'-ethyl-5,4'-ditert.butyloxanilide, and mixtures of ortho- and paramethoxy- as well as of o- and p-ethoxy-disubstituted oxanilides.

3. Metal deactivators such as, for example, oxanilide, isophthalic acid dihydrazide, sebacic acid-bis-phenylhydrazide, bis-benzylidene-oxalic acid dihydrazide, N,N'-diacetyl-adipic acid dihydrazide, N,N'-bis-salicyloyloxalic acid dihydrazide, N,N'-bis-salicyloyl-hydrazine and N,N'-bis-(3,5-ditert.butyl-4-hydroxyphenylpropionyl)-hydrazine.

4. Phosphites such as, for example, triphenylphosphite, diphenyl-alkylphosphites, phenyl-dialkylphosphites, tri-(nonylphenyl)-phosphite, trilaurylphosphite, trioctadecylphosphite, 3,9-di-isodecyloxy-2,4,8,10-tetraoxa-3,9-diphospha-spiro[5,5]undecane and tri-(4-hydroxy-3,5-ditert.butylphenyl)-phosphite.

5. Compounds breaking down peroxide, such as, for example, esters of β-thio-dipropionic acid, for example, of lauryl, stearyl, myrystyl or tridecyl esters, salts of 2-mercaptobenzimidazole, for example, Zn-salt, and diphenylthiourea.

6. Polyamide stabilisers such as, for example, copper salts in combination with iodides and/or phosphorus compounds and salts of bivalent manganese.

7. Basic co-stabilisers such as, for example, melamine, benzoguanamine, polyvinylpyrrolidone, dicyanodiamide, triallylcyanurate, urea derivatives, hydrazine derivatives, amines, polyamides, polyurethanes, alkali metal salts alkaline earth metal salts of higher fatty acids such as, for example, calcium stearate, zinc stearate, magnesium stearate, sodium ricinoleate or potassium palmitate.

8. PVC Stabilisers such as, for example, organic tin compounds, organic lead compounds and Ba/Cd salts of fatty acids.

9. Nucleating agents such as, for example, 4-tert.butylbenzoic acid, adipic acid and diphenylacetic acid.

10. Other additives such as, for example, plasticisers, lubricants, emulsifiers, fillers, carbon black, asbestos, kaolin, talcum, glass fibres, pigments, optical brighteners, flameproofing agents and antistatic agents.

Compounds of formula I can be obtained by process A, B or C.

A. Sulphones of the general formulae

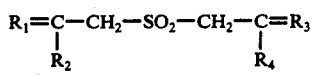

or

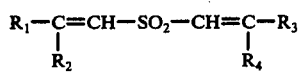

in which $R_1$, $R_2$, $R_3$ and $R_4$ have the meanings given under formula I, are cyclised with ammonia, or with a primary amine of the formula $NH_2X$ wherein X represents unsubstituted alkyl, substituted alkyl, alkenyl, alkynyl or aralkyl, to compounds of formula I. The reaction can be performed at a temperature of between 20° and 150° C, preferably between 60° and 100° C, with or without solvents.

The sulphones used as starting compounds are obtained from the corresponding thioethers by oxidation with hydrogen peroxide by application of methods known per se [see H. J. Backer et al. Rec. 67, 456 (1948)].

B. Compounds of formula I substituted on the nitrogen atom can be obtained from compounds of the formula

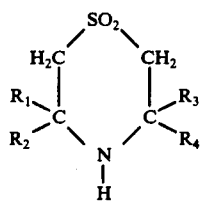

by alkylation, acylation, halogenation, nitrosation and reduction of the N-nitroso compounds, or oxidation, with the use of known methods.

C. Compounds of the formula

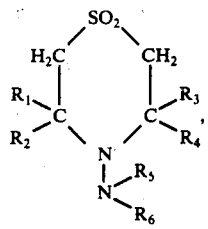

wherein $R_1$ to $R_6$ have the same meanings as under formula I, can be obtained from compounds of the formula

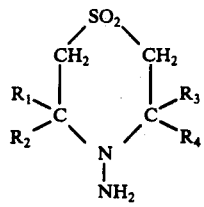

by alkylation or acylation, using known methods.

As already mentioned, further additives can be used with the compounds of formula I in stabiliser systems. Preferred among these systems are those consisting of at least one compound of formula I and at least one co-stabliser from the class of UV-absorbers and agents protecting against light rays, such as, for example, 2-hydroxybenzophenones, 2-(2'-hydroxyphenyl)benzotriazoles, oxalic acid diamides, aryl esters of an unsubstituted or substituted benzoic acid or acrylates.

These stabiliser systems can stabilise organic substrates such as, for example, polymers. They are preferably used, however, in styrene polymers.

Styrene polymers, particularly styrene copolymers such as SAN (styrene-acrylonitrile), ASA (acrylonitrilestyrene-acrylic ester) and, in particular, ABS (acrylonitrilebutadiene-styrene) are being employed, on account of their well-balanced mechanical properties and outstanding workability, to an increasing extent in numerous fields of application. Examples of these are as follows: housings and parts of housings for electrical equipment, internal parts of refrigerators, telephones, and also heating and ventilation equipment and linings and covers for cars. Such plastics are moreover being used to an ever increasing degree for outside purposes, e.g. in boat construction, for the bodywork of motorcars and for caravan accessories.

A factor preventing a wide general application of these cheap plastics is, however, their inadequate weather resistance. For example, ABS articles suffer after only a few weeks of exposure to the weather a marked deterioration of mechanical properties.

There has therefore been no lack of attempts to improve the ageing resistance of styrene copolymers on exposure to the weather. These measures include, for example, the laminating of ABS-sheets with pigmented and/or UV-stabilised polyacrylate films, the application of protective acrylic-resin-lacquer top layers, or the addition of relatively large amounts of carbon black. A certain degree of weather resistance can also be obtained by the addition of UV-absorbers, for example, of the benzophenone or benzotriazole type.

These known methods for the improvement of resistance to ageing are, however, inadequately effective and have technical disadvantages. Thus, lamination with protective layers is possible only in the case of sheets that are further processed, for example, in the deep-drawing process, and is not transferable to injection moulded parts. The surface protection effected by lacquering requires an additional step in processing, which leads to an increase in costs. An addition of carbon black, on the other hand, produces an undesirable blackening of the articles.

Accordingly, a sustained improvement in weather resistance by virtue of the addition of non-discolouring additives would be the ideal solution to the problem, since there would then no longer exist limitations with regard to colour and the processing possibilities of styrene polymers.

It has now been found that the stabiliser systems, preferably such ones consisting of a. at least one compound of formula I and
b. at least one co-stabiliser of formulae II, III, IV, V, VI. VII or VIII

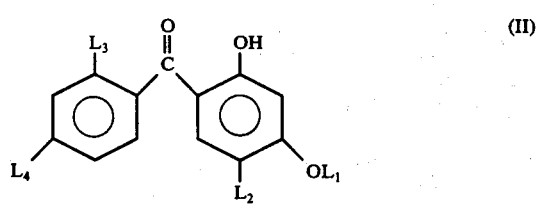

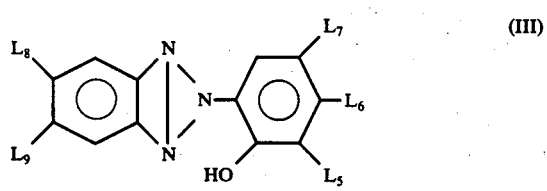

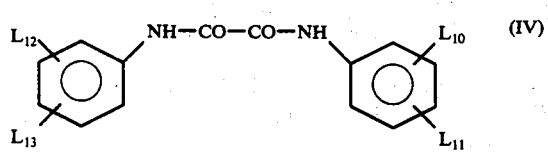

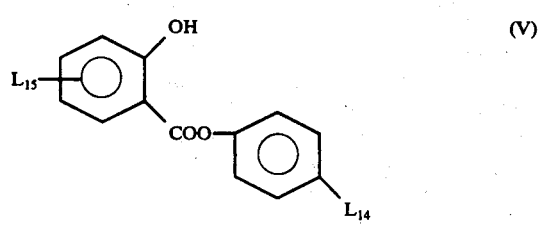

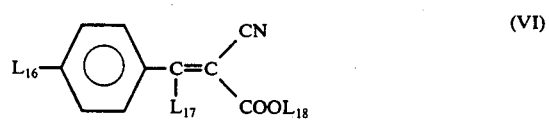

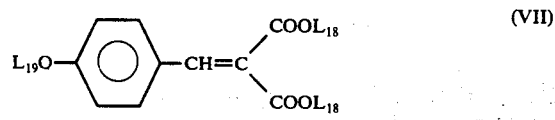

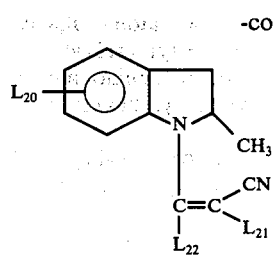

wherein the symbols have the following meanings:

$L_1$ hydrogen, alkyl, alkenyl or aralkyl,
$L_2$ hydrogen, alkyl or chlorine,
$L_3$ hydrogen, hydroxy, carboxy, alkoxy or alkyl,
$L_4$ hydrogen, hydroxy, alkoxy, alkenyloxy, aralkoxy or alkyl,
$L_5$ hydrogen, alkyl, alkenyl, cycloalkyl, aralkyl, aryl, acylamino, acylaminoalkyl or halogen,
$L_6$ hydrogen, alkyl, hydroxy, alkoxy or acylamino,
$L_7$ hydrogen, alkyl, alkenyl, cycloalkyl, aralkyl, aryl, alkoxy, halogen, carboxy, alkoxycarbonyl, alkoxycarbonylalkyl or acylamino,
$L_8$ hydrogen, alkyl, hydroxy, alkoxy, halogen, acylamino, carboxy, alkoxycarbonyl, acyloxy, carbamoyl, alkoxysulphonyl, aryloxysulfonyl or sulphonamido,
$L_9$ hydrogen, alkyl or halogen,
$L_{10}$ and $L_{12}$ each independently represent hydrogen, alkyl, alkoxy, alkenyloxy, aralkoxy, aryloxy, halogen or alkoxycarbonyl,
$L_{11}$ and $L_{13}$ each independently represent hydrogen or alkyl,
$L_{14}$ and $L_{15}$ each independently represent hydrogen, alkyl, cycloalkyl or aralkyl,
$L_{16}$ hydrogen, alkoxy or aralkoxy,
$L_{17}$ alkyl or aryl,
$L_{18}$ alkyl, cycloalkyl or aralkyl,
$L_{19}$ alkyl or aralkyl,
$L_{20}$ hydrogen, alkyl, alkoxy or halogen,
$L_{21}$ cyano or alkoxycarbonyl, and
$L_{22}$ hydrogen or alkyl, improve in an unexpectedly sustained manner the weather resistance of styrene polymers.

The said stabiliser systems render possible the effective protection of styrene polymers, particularly styrene copolymers, such as, for example, ABS-plastics, against the harmful effect of UV-radiation, heat and oxygen, without discolouration of the styrene polymers stabilised with these stabiliser systems. Furthermore, plastics therewith stabilised can be remoulded by all the usual processing methods, and require no aftertreatment for the purpose of applying protective covering layers.

Part (b) of the stabiliser system according to the invention consists preferably of at least one co-stabiliser of formulae II and VIII wherein the symbols have the following meanings:

$L_1$ hydrogen, alkyl having 1-18 carbon atoms, allyl, methallyl or benzyl,
$L_2$ hydrogen,
$L_3$ hydrogen or hydroxy,
$L_4$ hydrogen, hydroxy, alkoxy having 1-20 carbon atoms, allyloxy, methallyloxy or benzyloxy, $L_5$ hydrogen, alkyl having 1-12 carbon atoms, alkenyl having 3-12 carbon atoms, cyclohexyl, aralkyl having 7-11 carbon atoms, phenyl, acylamino having 2-12 carbon atoms, acylaminomethyl having 3-13 carbon atoms, chlorine or bromine, $L_6$ hydrogen, methyl, hydroxy, alkoxy having 1-12 carbon atoms or acylamino having 2-12 carbon atoms, $L_7$ hydrogen, alkyl having 1-12 carbon atoms, aralkyl having 7-11 carbon atoms, cyclohexyl, phenyl, alkoxy having 1-12 carbon atoms, chlorine, bromine, carboxy, alkoxycarbonyl having 2-13 carbon atoms, alkoxycarbonylalkyl having 3-14 carbon atoms or acylamino having 2-12 carbon atoms, $L_8$ hydrogen, alkyl having 1-8 carbon atoms, alkoxy having 1-12 carbon atoms, chlorine, bromine, acylamino having 2-12 carbon atoms, carboxy, alkoxycarbonyl having 2-13 carbon atoms, acyloxy having 2-12 carbon atoms, carbamoyl having 3-17 carbon atoms, alkoxysulphonyl having 1-12 carbon atoms, phenoxysulphonyl or sulphoneamido having 2-16 carbon atoms, $L_9$ hydrogen, methyl, chlorine or bromine, $L_{10}$ and $L_{12}$ each independently represent alkyl having 1-8 carbon atoms, alkoxy having 1-12 carbon atoms, allyloxy, methallyloxy, phenoxy, benzyloxy, chlorine, bromine or alkoxycarbonyl having 2-13 carbon atoms, $L_{11}$ and $L_{13}$ each independently represent hydrogen or alkyl having 1-18 carbon atoms, $L_{14}$ and $L_{15}$ each independently represent hydrogen or alkyl having 1-12 carbon atoms, $L_{16}$ alkoxy having 1-12 carbon atoms, $L_{17}$ alkyl having 1-3 carbon atoms or phenyl, $L_{18}$ alkyl having 1-12 carbon atoms, $L_{19}$ alkyl having 1-12 carbon atoms, $L_{20}$ hydrogen, alkyl having 1-8 carbon atoms, alkoxy having 1-18 carbon atoms or chlorine, $L_{21}$ cyano or alkoxycarbonyl having 2-20 carbon atoms, and $L_{22}$ hydrogen or alkyl having 1-3 carbon atoms.

Part b of the stabiliser system according to the invention consists particularly preferably of at least one co-stabiliser of formulae II to VIII wherein the symbols have the following meanings:

$L_1$ hydrogen, alkyl having 1-12 carbon atoms or benzyl,
$L_2$ hydrogen,
$L_3$ hydrogen or hydroxy,
$L_4$ hydrogen, hydroxy or alkoxy having 1-12 carbon atoms,
$L_5$ hydrogen, alkyl having 1-8 carbon atoms, allyl, methallyl, phenyl, benzyl, α-phenethyl, α-phenylisopropyl, acylaminomethyl having 3-9 carbon atoms or chlorine,
$L_6$ hydrogen, methyl, hydroxy or alkoxy having 1-8 carbon atoms,
$L_7$ hydrogen, alkyl having 1-8 carbon atoms, cyclohexyl, phenyl, benzyl, α-phenethyl, α-phenylisopropyl or chlorine,
$L_8$ hydrogen or methyl,
$L_9$ hydrogen,
$L_{10}$ and $L_{12}$ each independently represent alkyl having 1-4 carbon atoms, alkoxy having 1-8 carbon atoms or chlorine,
$L_{11}$ and $L_{13}$ each independently represent hydrogen or alkyl having 1-4 carbon atoms,
$L_{14}$ hydrogen or alkyl having 1-8 carbon atoms,
$L_{15}$ hydrogen,
$L_{16}$ alkoxy having 1-4 carbon atoms,
$L_{17}$ methyl or phenyl,
$L_{18}$ alkyl having 1-8 carbon atoms,
$L_{19}$ alkyl having 1-4 carbon atoms,
$L_{20}$ hydrogen,
$L_{21}$ alkoxycarbonyl having 2-5 carbon atoms, and
$L_{22}$ hydrogen.

Teil (b) of the stabiliser system according to the invention consists even more preferably of at least one co-stabiliser of formulae II, III or IV wherein the symbols have the following meaning:

$L_1$ hydrogen, alkyl having 1-12 carbon atoms or benzyl,
$L_2$ hydrogen,
$L_3$ hydrogen or hydroxy,
$L_4$ hydrogen, hydroxy or alkoxy having 1-12 carbon atoms,
$L_5$ hydrogen, alkyl having 1-8 carbon atoms, allyl, methallyl, phenyl, benzyl, α-phenethyl, α-phenylisopropyl, acylaminomethyl having 3-9 carbon atoms or chlorine,
$L_6$ hydrogen, methyl, hydroxy or alkoxy having 1-8 carbon atoms,
$L_7$ hydrogen, alkyl having 1-8 carbon atoms, cyclohexyl, phenyl, benzyl, α-phenethyl, α-phenylisopropyl or chlorine,
$L_8$ hydrogen or methyl,
$L_9$ hydrogen,
$L_{10}$ and $L_{12}$ each independently represent alkyl having 1-4 carbon atoms, alkoxy having 1-8 carbon atoms or chlorine, and
$L_{11}$ and $L_{13}$ each independently represent hydrogen or alkyl having 1 to 4 carbon atoms.

If $L_1$, $L_2$, $L_3$, $L_4$, $L_5$, $L_6$, $L_7$, $L_8$, $L_9$, $L_{10}$, $L_{11}$, $L_{12}$, $L_{13}$, $L_{14}$, $L_{15}$, $L_{17}$, $L_{18}$, $L_{19}$, $L_{20}$ and $L_{22}$ represent alkyl, then within the scope of the given limits they are, for example, methyl, ethyl, propyl, butyl, pentyl, hexyl, octyl, decyl, dodecyl, tetradecyl, octadecyl, eicosyl, iso-propyl, iso-butyl, tert.butyl, iso-pentyl, tert.amyl, iso-octyl or tert.octyl.

If $L_1$, $L_5$ and $L_7$ represent alkenyl, then within the scope of the given limits they are, for example, allyl, methallyl, 3-hexenyl, 4-octenyl or 10-undecenyl.

If $L_5$, $L_7$ and $L_{17}$ represent aryl, then they can be phenyl. If $L_1$, $L_5$, $L_7$, $L_{14}$, $L_{15}$, $L_{18}$ and $L_{19}$ represent aralkyl, then within the scope of the given limits they can be, for example, benzyl, α-methylbenzyl, α,α-dimethylbenzyl or naphthyl-1-methyl.

If $L_5$, $L_7$, $L_{14}$, $L_{15}$ and $L_{18}$ represent cycloalkyl, then they are, for example, cyclohexyl or cyclooctyl.

If $L_5$ represents acylaminoalkyl, then this is, for example, acetyl, propionyl, butyroyl, 2-ethylhexanoyl or lauroylaminomethyl, or the radical of the formula

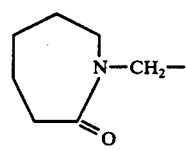

If $L_7$ represents alkoxycarbonylalkyl, then within the scope of the given limits this is, for example, 2-methoxycarbonylethyl, 2-ethoxycarbonylethyl, 2-butoxycarbonylethyl, hexyloxycarbonylmethyl, methoxycarbonylpropyl, 2-dodecyloxycarbonylethyl, 2-octadecyloxycarbonylethyl or 2-eicoyloxycarbonylethyl.

If $L_7$, $L_8$, $L_{10}$, $L_{12}$ and $L_{21}$ represent alkoxycarbonyl, then within the scope of the given limits they are, for example, methoxy-, ethoxy-, propoxy-, butoxy-, isobutoxy-, pentyloxy-, hexyloxy-, octoxy- or dodecyloxycarbonyl.

If $L_3$, $L_4$, $L_6$, $L_7$, $L_8$, $L_{10}$, $L_{12}$, $L_{16}$ and $L_{20}$ represent alkoxy, then within the scope of the given limits they are, for example, methoxy, ethoxy, propoxy, butoxy, β-methoxyethoxy, pentyloxy, iso-butoxy, octoxy, dodecyloxy, tetradecyloxy, octadecyloxy or eicosyloxy.

If $L_4$, $L_{10}$, $L_{12}$ and $L_{16}$ represent aralkoxy, then they can be benzyloxy or 4-tert.butylbenzyloxy.

If $L_4$, $L_{10}$ and $L_{12}$ are alkenyloxy, then they can be allyloxy or methallyloxy.

As aryloxy, $L_{10}$ and $L_{12}$ can be phenoxy.

If $L_8$ represents acyloxy, then within the scope of the given limits it is, for example, acetoxy, propionyloxy, butyroyloxy, 2-ethylhexanoyloxy or lauryloxy.

If $L_5$, $L_6$, $L_7$ and $L_8$ represent acylamino, then within the scope of the given limits they are, for example, acetyl-, propionyl-, butyroyl-, pentanoyl-, 2-ethylhexanoyl-, lauroyl-, stearoyl-, phenylacetyl-, acryloyl-, methacryloyl- or cyclohexylcarbonylamino.

If $L_8$ represents aryloxysulphonyl, carbamoyl, alkoxysulphonyl or sulphoamide, then within the scope of the given limits it is, for example, N,N-dimethyl-, N,N-diethyl-, N-butyl-, N-octyl- or N,N-dioctylcarbamoyl or -sulphonamido, methoxysulphonyl, ethoxysulphonyl, butoxysulphonyl, octoxysulphonyl, dodecyloxysulphonyl or phenoxysulphonyl.

As halogen, $L_5$, $L_7$, $L_8$, $L_9$, $L_{10}$, $L_{12}$ and $L_{20}$ can be chlorine.

The said stabiliser systems contain, for example, the following compounds of formula I:

I. 1. 2,6-dimethyl-2,6-diethyl-1-aza-4-thiacyclohexane-4,4-dioxide,
I. 2. 2,2,6,6-tetramethyl-1-aza-4-thiacyclohexane-4,4-dioxide,
I. 3. 2,2-dimethyl-6,6-pentylene-1-aza-4-thiacyclohexane-4,4-dioxide,
I. 4. 1,2,2,6-tetramethyl-6-isopropyl-1-aza-4-thiacyclohexane-4,4-dioxide,
I. 5. 2,2-pentylene-6,6-pentylene-1-aza-4-thiacyclohexane-4,4-dioxide,
I. 6. 2,2,6-trimethyl-6-n-butyl-1-aza-4-thiacyclohexane-4,4-dioxide,
I. 7. 1,2,2,6,6-pentamethyl-1-aza-4-thiacyclohexane-4,4-dioxide,
I. 8. 1-n-propyl-2,2,6,6-tetramethyl-1-aza-4-thiacyclohexane-4,4-dioxide,
I. 9. 1-iso-butyl-2,2,6,6-tetramethyl-1-aza-4-thiacyclohexane-4,4-dioxide,
I. 10. 1-carbethoxymethyl-2,2,6,6-tetramethyl-1-aza-4-thiacyclohexane-4,4-dioxide,
I. 11. 1-(2'-hydroxyethyl)-2,2,6,6-tetramethyl-1-aza-4-thiacyclohexane-4,4-dioxide,
I. 12. 1-(2'-phenyl-2'-hydroxyethyl)-2,2,6,6-tetramethyl-1-aza-4-thiacyclohexane-4,4-dioxide,
I. 13. 1-acetoxyethyl-2,2,6,6-tetramethyl-1-aza-4-thiacyclohexane-4,4-dioxide,
I. 14. 1-(2'-phenyl-2'-acetoxyethyl)-2,2,6,6-tetramethyl-1-aza-4-thiacyclohexane-4,4-dioxide,
I. 15. 1-octylamino-2,2,6,6-tetramethyl-1-aza-4-thiacyclohexane-4,4-dioxide,
I. 16. 1-dimethylamino-2,2,6,6-tetramethyl-1-aza-4-thiacyclohexane-4,4-dioxide,
I. 17. 1-diethylamino-2,2,6,6-tetramethyl-1-aza-4-thiacyclohexane-4,4-dioxide,
I. 18. 1-acetyl-methylamino-2,2,6,6-tetramethyl-1-aza-4-thiacyclohexane-4,4-dioxide,
I. 19. 1-octanoylamino-2,2,6,6-tetramethyl-1-aza-4-thiacyclohexane-4,4-dioxide,
I. 20. 1-lauroylamino-2,2,6,6-tetramethyl-1-aza-4-thiacyclohexane-4,4-dioxide,
I. 21. 1-ethoxycarbonylamino-2,2,6,6-tetramethyl-1-aza-4-thiacyclohexane-4,4-dioxide,
I. 22. 1-octyl-2,2,6,6-tetramethyl-1-aza-4-thiacyclohexane-4,4-dioxide,
I. 23. 1-amino-2,2,6,6-tetramethyl-1-aza-4-thiacyclohexane-4,4-dioxide,
I. 24. 1-dodecyl-2,2,6,6-tetramethyl-1-aza-4-thiacyclohexane-4,4-dioxide,
I. 25. 1-allyl-2,2,6,6-tetramethyl-1-aza-4-thiacyclohexane-4,4-dioxide,
I. 26. 1-propargyl-2,2,6,6-tetramethyl-1-aza-4-thiacyclohexane-4,4-dioxide,
I. 27. 1-benzyl-2,2,6,6-tetramethyl-1-aza-4-thiacyclohexane-4,4-dioxide,
I. 28. 1-(4-tert.butylbenzyl)-2,2,6,6-tetramethyl-1-azathiacyclohexane-4,4-dioxide,
I. 29. 2,2,6,6-tetramethyl-1-aza-4-thiacyclohexane-1,4,4-trioxide,
I. 30. 1-butyl-2,2,6,6-tetramethyl-1-aza-4-thiacyclohexane-4,4-dioxide,
I. 31. 1-benzoylamino-2,2,6,6-tetramethyl-1-aza-4-thiacyclohexane-4,4-dioxide,
I. 32. 1-acetylamino-2,2,6,6-tetramethyl-1-aza-4-thiacyclohexane-4,4-dioxide,
I. 33. 1-cyanomethyl-2,2,6,6-tetramethyl-1-aza-4-thiacyclohexane-4,4-dioxide,
I. 34. 1-(β-cyanoethyl)-2,2,6,6-tetramethyl-1-aza-4-thiacyclohexane-4,4-dioxide.

Examples of compounds of formula II are:

II. 1. 2,4-dihydroxy-,
II. 2. 2-hydroxy-4-methoxy-,
II. 3. 2-hydroxy-4-octoxy-,
II. 4. 2-hydroxy-4-dodecyloxy-,
II. 5. 2-hydroxy-4-benzyloxy-,
II. 6. 2-hydroxy-4,4'-dimethoxy-,
II. 7. 2,4,4'-trihydroxy-,
II. 8. 2,2'-dihydroxy-4,4'-dimethoxy-,
II. 9. 2,2',4,4'-tetrahydroxy-,
II. 10. 2,2'-dihydroxy-4-methoxy-,
II. 11. 2-hydroxy-2'-carboxy-4-methoxy-,
II. 12. 2,2'-dihydroxy-4-octoxy- and
II. 13. 2,2'-dihydroxy-4-dodecyloxy-benzophenone.

Examples of compounds of formula III are:

III. 1. 2-(2-hydroxy-5-methylphenyl)-,
III. 2. 2-(2-hydroxy-5-tert.butylphenyl)-,
III. 3. 2-(2-hydroxy-5-tert.-octylphenyl)-,
III. 4. 2-(2-hydroxy-3-tert.butyl-5-methylphenyl)-,
III. 5. 2-(2-hydroxy-3-tert.butyl-5-methylphenyl)-5-chloro-,
III. 6. 2-(2-hydroxy-3,5-ditert.butylphenyl)-,
III. 7. 2-(2-hydroxy-3,5-di-tert.butylphenyl)-5-chloro-,
III. 8. 2-(2-hydroxy-3,5-di-tert.-amylphenyl)-, III. 9. 2-(2-hydroxy-3,5-di-tert.amylphenyl)-5-chloro-,
III. 10. 2-(2-hydroxy-3-sec.butyl-5-tert.-butylphenyl)-,
III. 11. 2-(2-hydroxy-3-tert.butyl-5-sec.-butylphenyl)-,
III. 12. 2-(2,4-dihydroxyphenyl)-,
III. 13. 2-(2-hydroxy-4-methoxyphenyl)-,
III. 14. 2-(2-hydroxy-4-octoxyphenyl)-,
III. 15. 2-(2-hydroxy-3-α-phenylethyl-5-methylphenyl)- and
III. 16. 2-(2-hydroxy-3-α-phenylethyl-5-methylphenyl)-5-chlorobenzotriazole.

Examples of compounds of formula IV are:

IV. 1. 2-ethyl-2'-ethoxy-,
IV. 2. 2-ethyl-2'-ethoxy-5'-tert.butyl-,
IV. 3. 2-ethyl-4-tert.butyl-2'-ethoxy-5'-tert.butyl-,
IV. 4. 2,2'-dimethoxy-,
IV. 5. 2,2'-diethoxy-,
IV. 6. 4,4'-dimethoxy-,
IV. 7. 4,4'-diethoxy-,
IV. 8. 2,4'-dimethoxy-,
IV. 9. 2,4'-diethoxy-,
IV. 10. 2-methoxy-2'-ethoxy-,
IV. 11. 2-methoxy-4'-ethoxy-,
IV. 12. 2-ethoxy-4-methoxy-,
IV. 13. 2,2'-dioctoxy-5,5'-di-tert.butyl-,
IV. 14. 2,2'-didodecyloxy-5,5'-di-tert.butyl-,
IV. 15. 2-ethyl-2'-octoxy-,
IV. 16. 4,4'-di-octoxy-,
IV. 17. 2-ethyl-2'-butoxy- and
IV. 18. 4-methyl-4'-methoxy-oxalanilide.

Examples of compounds of formula V are:

V. 1. salicyclic acid phenyl ester,
V. 2. salicylic acid-4-tert.butylphenyl ester,
V. 3. salicylic acid-4-tert.octylphenyl ester.

Examples of compounds of formula VI are:

VI. 1. α-cyano-β-methyl-4-methoxycinnamic acid methyl ester,
VI. 2. α-cyano-β-methyl-4-methoxycinnamic acid butyl ester,
VI. 3. α-cyano-β-phenyl-cinnamic acid ethyl ester,
VI. 4. α-cyano-β-phenyl-cinnamic acid isooctyl ester.

Examples of compounds of formula VII are:

VII. 1. 4-methoxy-benzylidenemalonic acid dimethyl ester,
VII. 2. 4-methoxy-benzylidenemalonic acid diethyl ester,
VII. 3. 4-butoxy-benzylidinemalonic acid dimethyl ester.

Examples of compounds of formula VIII are:

VIII. 1. N-(β-cyano-β-carbomethoxyvinyl)-2-methylindoline,
VIII. 2. N-(β-cyano-β-carbooctoxyvinyl)-2-methylindoline,
VIII. 3. N-(β-cyano-β-carbethoxyvinyl)-2-methylindoline,
VIII. 4. N-(β-cyano-β-carboisooctoxyvinyl)-2-methylindoline.

Examples of stabiliser systems are:

2-hydroxy-4-methoxybenzophenone and
2,2,6,6-tetramethyl-1-aza-4-thiacyclohexane-4,4-dioxide,
2-hydroxy-4-octoxybenzophenone and
2,2,6,6-tetramethyl-1-aza-4-thiacyclohexane-4,4-dioxide,
2-(2-hydroxy-5-methylphenyl)-benzotriazole and
2,2,6,6-tetramethyl-1-aza-4-thiacyclohexane-4,4-dioxide,
2-(2-hydroxy-3,5-di-tert.butylphenyl)-benzotriazole and
2,2,6,6-tetramethyl-1-aza-4-thiacyclohexane-4,4-dioxide,
2-(2-hydroxy-3-tert.butyl-5-methylphenyl)-5-chlorobenzotriazole and 2,2,6,6-tetramethyl-1-aza-4-thiacyclohexane-4,4-dioxide,
2-(2-hydroxy-3,5-di-tert.butylphenyl)-5-chlorobenzotriazole and
2,2,6,6-tetramethyl-1-aza-4-thiacyclohexane-4,4-dioxide,
2-ethyl-2'-ethoxy-oxalanilide and
2,2,6,6-tetramethyl-1-aza-4-thiacyclohexane-4,4-dioxide,
2-ethyl-2'-ethoxy-5'-tert.butyl-oxalanilide and
2,2,6,6-tetramethyl-1-aza-4-thiacyclohexane-4,4-dioxide,
2-hydroxy-4-methoxybenzophenone and
1-amino-2,2,6,6-tetramethyl-1-aza-4-thiacyclohexane-4,4-dioxide,
2-hydroxy-4-octoxybenzophenone and
1-amino-2,2,6,6-tetramethyl-1-aza-4-thiacyclohexane-4,4-dioxide,
2-(2-hydroxy-5-methylphenyl)-benzotriazole and
1-amino-2,2,6,6-tetramethyl-1-aza-4-thiacyclohexane-4,4-dioxide,
2-(2-hydroxy-3,5-di-tert.butylphenyl)-benzotriazole and
1-amino-2,2,6,6-tetramethyl-1-aza-4-thiacyclohexane-4,4-dioxide,
2-(2-hydroxy-3-tert.butyl-5-methylphenyl)-5-chlorobenzotriazole
and 1-amino-2,2,6,6-tetramethyl-1-aza-4-thiacyclohexane-4,4-dioxide,
2-(2-hydroxy-3,5-di-tert.butylphenyl)-5-chlorobenzotriazole and
1-amino-2,2,6,6-tetramethyl-1-aza-4-thiacyclohexane-4,4-dioxide,
2-ethyl-2'-ethoxy-oxalanilide and
1-amino-2,2,6,6-tetramethyl-1-aza-4-thiacyclohexane-4,4-dioxide,
2-ethyl-2'-ethoxy-5'-tert.butyl-oxalanilide and
1-amino-2,2,6,6-tetramethyl-1-aza-4-thiacyclohexane-4,4-dioxide,
2-hydroxy-4-methoxybenzophenone and
1-octyl-2,2,6,6-tetramethyl-1-aza-4-thiacyclohexane-4,4-dioxide,
2-hydroxy-4-octoxybenzophenone and
1-octyl-2,2,6,6-tetramethyl-1-aza-4-thiacyclohexane-4,4-dioxide,
2-(2-hydroxy-5-methylphenyl)-benzotriazole and
1-octyl-2,2,6,6-tetramethyl-1-aza-4-thiacyclohexane-4,4-dioxide,
2-(2-hydroxy-3,5-di-tert.butylphenyl)-benzotriazole and
1-octyl-2,2,6,6-tetramethyl-1-aza-4-thiacyclohexane-4,4-dioxide,
2-(2-hydroxy-3-tert.butyl-5-methylphenyl)-5-chlorobenzotriazole
and 1-octyl-2,2,6,6-tetramethyl-1-aza-4-thiacyclohexane-4,4-dioxide, 2-(2-hydroxy-3,5-di-tert.butylphenyl)-5-chlorobenzo-
  triazole and
1-octyl-2,2,6,6-tetramethyl-1-aza-4-thiacyclohexane-
  4,4-dioxide,
2-ethyl-2'-ethoxy-oxalanilide and
1-octyl-2,2,6,6-tetramethyl-1-aza-4-thiacyclohexane-
  4,4-dioxide,
2-ethyl-2'-ethoxy-5'-tert.butyl-oxalanilide and
1-octyl-2,2,6,6-tetramethyl-1-aza-4-thiacyclohexane-
  4,4-dioxide,
2-hydroxy-4-methoxybenzophenone and
1,2,2,6,6-pentamethyl-1-aza-4-thiacyclohexane-4,4-
  dioxide,
2-hydroxy-4-octoxybenzophenone and
1,2,2,6,6-pentamethyl-1-aza-4-thiacyclohexane-4,4-
  dioxide,
2-(2-hydroxy-5-methylphenyl)-benzotriazole and
1,2,2,6,6-pentamethyl-1-aza-4-thiacyclohexane-4,4-
  dioxide,
2-(2-hydroxy-3,5-di-tert.butylphenyl)-benzotriazole and
1,2,2,6,6-pentamethyl-1-aza-4-thiacyclohexane-4,4-
  dioxide,
2-(2-hydroxy-3-tert.butyl-5-methylphenyl)-5-
  chlorobenzotriazole
and 1,2,2,6,6-pentamethyl-1-aza-4-thiacyclohexane-4,4-
  dioxide,
2-(2-hydroxy-3,5-di-tert.butylphenyl)-5-chlorobenzo-
  triazole
and 1,2,2,6,6-pentamethyl-1-aza-4-thiacyclohexane-4,4-
  dioxide,
2-ethyl-2'-ethoxy-oxalanilide and
1,2,2,6,6-pentamethyl-1-aza-4-thiacyclohexane-4,4-
  dioxide,
2-ethyl-2'-ethoxy-5'-tert.butyl-oxalanilide and
1,2,2,6,6-pentamethyl-1-aza-4-thiacyclohexane-4,4-
  dioxide,
2-hydroxy-4-methoxybenzophenone and
1-lauroyl-2,2,6,6-tetramethyl-1-aza-4-thiacyclohexane-
  4,4-dioxide,
2-hydroxy-4-octooxybenzophenone and
1-lauroylamino-2,2,6,6-tetramethyl-1-aza-4-thiacy-
  clohexane-4,4-dioxide,
2-(2-hydroxy-5-methylphenyl)-benzotriazole and
1-lauroylamino-2,2,6,6-tetramethyl-1-aza-4-thiacy-
  clohexane-4,4-dioxide,
2-(2-hydroxy-3,5-di-tert.butylphenyl)-benzotriazole and
1-lauroylamino-2,2,6,6-tetramethyl-1-aza-4-thiacy-
  clohexane-4,4-dioxide,
2-(2-hydroxy-3-tert.butyl-5-methylphenyl)-5-
  chlorobenzotriazole and
1-lauroylamino-2,2,6,6-tetramethyl-1-aza-4-thiacy-
  clohexane-4,4-dioxide,
2-(2-hydroxy-3,5-di-tert.butylphenyl)-5-chlorobenzo-
  triazole and
1-lauroylamino-2,2,6,6-tetramethyl-1-aza-4-thiacy-
  clohexane-4,4-dioxide,
2-ethyl-2'-ethoxy-oxalanilide and
1-lauroylamino-2,2,6,6-tetramethyl-1-aza-4-thiacy-
  clohexane-4,4-dioxide,
2-ethyl-2'-ethoxy-5'-tert.butyl-oxalanilide and
1-lauroylamino-2,2,6,6-tetramethyl-1-aza-4-thiacy-
  clohexane-4,4-dioxide.

Suitable carrier materials for the stabiliser systems are preferably the following:
polystyrene and impact-resistant polystyrenes modified with elastomers, styrene copolymers such as, for example, styrene-acrylonitrile-copolymers, and copolymers additionally containing copolymerisable monomers, such as, for example, styrene-acrylonitrile-methylmethacrylate-copolymers, styrene-acrylonitrile-butadiene-copolymers, styrene-acrylonitrile-acrylic ester copolymers, styrene-acrylonitrile-copolymers modified with acrylic ester polymerisates to render them impact-resistant, as well as styrene polymerisates modified with EPDM (ethylene-propylene-diene monomers) to render them impact-resistant. In the mentioned polymers, styrene can be completely or partially replaced by α-methylstyrene. Particularly valuable are the stabiliser systems for the stabilisation of styrene-acrylonitrile-butadiene-copolymers, which are in general designated as ABS-plastics, and which are described in detail in the book "ABS Resin Manufacture 1970" by C. Placek, Noyes Data Corporation, New Jersey. Numerous processes are known for the manufacture of the aforementioned styrene polymerisates, such as, for example, bulk polymerisation, and polymerisation in solution, emulsion or suspension, whereby several of these processes may be combined. Depending on the process employed, the incorporation of the stabiliser systems can be effected during one of the various process stages, such as, for example, during polymerisation, working up or compounding. If, for example, the emulsion process is being employed for polymerisation, then the stabiliser systems can be added in a suitably formulated emulsion or suspension, alone or in combination with other additives, before the precipitation of the latex. The various components of the stabiliser systems can also be added at different times during the manufacture of the styrene polymerisates. The stabiliser systems can also be added, for example, by dry mixing, before granulation, with the polymerisates to be stabilised. If the styrene polymerisates are already in granular form, then the stabiliser systems may be added by dry mixing before the processing of the material into finished components.

The weight ratio of the compounds of formula I to the compounds of formulae II – VIII can vary in the stabiliser systems within wide limits of, for example, 1 : 10 to 10 : 1. Preferably, this ratio varies within the limits of 2 : 1 to 1 : 2. Particularly preferred is a weight ratio of 1 : 1.

The stabiliser systems are added to the carrier materials in a concentration of 0.1–5 percent by weight, relative to the carrier material. Advantageously, the amount added is 0.5–4%, the amount particularly preferred being 0.5–2.5%.

The compounds of formulae II–VIII can be prepared in accordance with U.S. Pat. Nos. 3,006,959 and 3,043,797, the Swiss Pat. No. 355,947, the British Pat. No. 1,177,095, the French Pat. No. 1,318,102 and the German 'Auslegeschrift' 1,087,902 and the Dutch Pat. No. 6,708,332.

The invention is further illustrated in the following examples. Parts are expressed in parts by weight and percentages in percent by weight.

EXAMPLE 1

113 g of 30% hydrogen peroxide solution is added dropwise at 25°–30° C in ca. 2 hours to 142.3 g (1 mole) of dimethallylsulphide [for preparation see Ind. Eng. Chem. 33, 115 (1941)] in 100 ml of glacial acetic acid. The reaction mixture is subsequently stirred for 2 hours at 25°–30° C and then heated to 70°–75° C. At this temperature there is added in ca. 2 hours a second portion of 113 g of 30% hydrogen peroxide solution and stirring is maintained for 2 hours at 90° C. After cooling, the organic layer is separated, dried over sodium sulphate and distilled in vacuo. The resulting yield is 130 g of dimethallylsulphone; B.P.$_{11}$ = 132° C; M.P. 32° C.

EXAMPLE 2

174.3 g (1 mole) of dimethallylsulphone is fed with 1000 ml of 24% ammonia solution into a 2.5 liter enameled autoclave. The contents of the autoclave are heated as follows:

| Time | Temperature | Pressure |
| --- | --- | --- |
| 24 h | 60° C | 2 bar |
| 24 h | 80° C | 4 bar |
| 24 h | 100° C | 6 bar |

After cooling, the partially crystallised reaction product is filtered off under suction and the aqueous solution concentrated by evaporation to dryness. The concentration residue and crystals are recrystallised together from ligroin to obtain 165 g of 2,2,6,6-tetramethyl-1-aza-4-thiacyclohexane-4,4-dioxide(1) as colourless crystals, M.P. 108° C.

EXAMPLE 3

19.1 g (0.1 mole) of 2,2,6,6-tetramethyl-1-aza-4-thiacyclohexane-4,4-dioxide is refluxed with 30 ml of 37% formaldehyde solution and 7 ml of formic acid for 24 hours. After cooling, the reaction mixture is made alkaline with sodium hydroxide solution, and extracted four times with 50 ml of ether each time. The ether solution is dried over sodium sulphate, and then fully concentrated by evaporation. The resulting residue crystallises after a certain time. By recrystallisation from ligroin, there is then obtained 1,2,2,6,6-pentamethyl-1-aza-4-thiacyclohexane-4,4-dioxide (2); M.P. 128° C.

EXAMPLE 4

38.2 g (0.2 mole) of 2,2,6,6-tetramethyl-1-aza-4-thiacyclohexane-4,4-dioxide is heated with 13.7 g of n-butylbromide for 120 hours at 95°–100° C. After cooling, the contents of the flask are taken up in 300 ml of ether. The difficultly soluble hydrobromide of 2,2,6,6-tetramethyl-1-aza-4-thiacyclohexane-4,4-dioxide is separated by filtration, and the ether solution extracted twice with 100 ml of water each time, in order to remove the last traces of starting product or its hydrobromide. The ether solution is dried over sodium sulphate and then fully concentrated by evaporation. The residue is crystallised from ligroin to obtain 1-butyl-2,2,6,6-tetramethyl-1-aza-4-thiacyclohexane-4,4-dioxide, M.P. 180° C (3).

If, instead of n-butyl bromide, equivalent amounts of n-octyl bromide and n-dodecyl bromide are used, with the procedure otherwise as described above, then the products obtained are 1-octyl-2,2,6,6-tetramethyl-1-aza-4-thiacyclohexane-4,4-dioxide (4), M.P. 159° C, and 1-dodecyl-2,2,6,6-tetramethyl-1-aza-4-thiacyclohexane-4,4-dioxide (5), M.P. 144° C, respectively.

EXAMPLE 5

38.2 g (0.2 mole) of 2,2,6,6-tetramethyl-1-aza-4-thiacyclohexane-4,4-dioxide is heated with 12.1 g of allyl bromide for 80 hours at 65°–70° C. The unreacted allyl bromide is subsequently completely distilled off at 50°–60° C and 15 mm pressure. The residue obtained is processed as described under Example 4, and 1-allyl-2,2,6,6-tetramethyl-1-aza-4-thiacyclohexane-4,4-dioxide (6), M.P. 126° C, obtained.

If an equivalent amount of propargyl bromide is used instead of allyl bromide, with the procedure otherwise as described above, then the product obtained is 1-propargyl-2,2,6,6-tetramethyl-1-aza-4-thiacyclohexane-4,4-dioxide (7), M.P. 179° C.

EXAMPLE 6

5.7 g (0.03 mole) of 2,2,6,6-tetramethyl-1-aza-4-thiacyclohexane-4,4-dioxide is dissolved in 100 ml of methylene chloride. To this solution there is then added dropwise at 20° C in ca. 90 minutes a solution of 11.2 g of m-chloroperoxybenzoic acid in 100 ml of methylene chloride. The reaction is slightly exothermic. Stirring is subsequently maintained for 15 hours at room temperature, and the precipitated m-chlorobenzoic acid filtered off. The reddish coloured methylene chloride solution is extracted twice with 50 ml of 2N sodium hydroxide solution each time, and then with 50 ml of 2N hydrochloric acid, and subsequently dried over sodium sulphate. After the solvent has been distilled off, the residue is crystallised from ethanol to obtain 2,2,6,6-tetramethyl-1-aza-4-thiacyclohexane-1,4,4-trioxide (8) of the formula

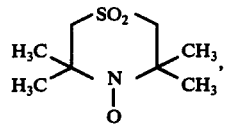

M.P. 163° C.

EXAMPLE 7

An amount of 7 ml of 50% sulphuric acid is added to 19.1 g (0.1 mole) of 2,2,6,6-tetramethyl-1-aza-4-thiacyclohexane-4,4-dioxide in 10 ml of water. An addition is then made dropwise in 1 hour, with good stirring, of a cold solution of 27.6 g of sodium nitrite in 40 ml of water. The nitrite precipitates in crystalline form. It is filtered off, and washed first with ether and then with ethyl acetate.

19.8 g of this nitrite is stirred with 2.5 g of sodium nitrite in 200 ml of 30% acetic acid for 5 hours at 85°–90° C. After cooling, the crystalline precipitate is filtered off and recrystallised from ethanol to obtain 1-nitroso-2,2,6,6-tetramethyl-1-aza-4-thiacyclohexane-4,4-dioxide (9), M.P. 184° C.

EXAMPLE 8

22.0 g (0.1 mole) of 1-nitroso-2,2,6,6-tetramethyl-1-aza-4-thiacyclohexane-4,4-dioxide is suspended in a mixture of 150 ml of glacial acetic acid and 100 ml of water. Within 3 hours, 40 g of zinc dust is introduced in small portions, the temperature being maintained between 30° and 35° C. The reaction mixture is subsequently fully stirred for 5 hours at 50° C; the zinc sediment is filtered off hot, and the cooled filtrate rendered alkaline with sodium hydroxide solution. It is extracted with ether, the ether solution dried over sodium sulphate, and the solvent evaporated off. Crystallisation of the residue from ligroin yields 1-amino-2,2,6,6-tetramethyl-1-aza-4-thiacyclohexane-4,4-dioxide (10), M.P. 122° C.

EXAMPLE 9

19.1 g (0.1 mole) of 2,2,6,6-tetramethyl-1-aza-4-thiacyclohexane-4,4-dioxide is added, with ice cooling, to 20 ml of 5N hydrochloric acid; 6.5 g of potassium cyanide is added and then in ca. 20 minutes, with good stirring, an addition made dropwise of 12.5 g of a 30% formaldehyde solution. The reaction mixture is subsequently stirred for 15 hours at 45° C. After cooling, the precipitate is filtered off under suction, washed with water, dried, and recrystallised from toluene/hexane to obtain 1-cyanomethyl-2,2,6,6-tetramethyl-1-aza-4-thiacyclohexane-4,4-dioxide (11), M.P. 188° C.

EXAMPLE 10

20.6 g (0.1 mole) of 1-amino-2,2,6,6-tetramethyl-1-aza-4-thiacyclohexane-4,4-dioxide is placed into 170 ml of toluene, and 14.1 g of benzoyl chloride added dropwise at 25° C, whereby the temperature rises to 38° C. Stirring is continued for 5 hours at 75° C, and the precipitated hydrochloride removed hot by filtration with suction. The filtrate is concentrated to half its amount by evaporation and then diluted with hexane. The product 1-benzoylamino-2,2,6,6-tetramethyl-1-aza-4-thiacyclohexane-4,4-dioxide (12) crystallises out as a colourless substance, M.P. 296° C.

EXAMPLE 11

19.1 g (0.1 mole) of 2,2,6,6-tetramethyl-1-aza-4-thiacyclohexane 4,4-dioxide is dissolved in 100 ml of water and 10 ml of 10N hydrochloric acid. The resulting solution is cooled to 0° C and within 90 minutes an addition made dropwise at between 0° and 5° C, with stirring, of 125 ml of a freshly prepared sodium hypochlorite solution (36 g of sodium hydroxide is dissolved in 300 ml of water, and at 0° C24 g of chlorine introduced). The reaction mixture is further stirred for 10 minutes at 0°-5° C; the precipitate is filtered off with suction, washed with water, dried, and crystallised from ligroin to yield 1-chloro-2,2,6,6-tetramethyl-1-aza-4-thiacyclohexane-4,4-dioxide (13) as colourless crystals, M.P. 163° C.

If an equivalent amount of sodium hypobromite solution is used instead of sodium hypochlorite, then 1-bromo-2,2,6,6-tetramethyl-1-aza-4-thiacyclohexane-4,4-dioxide (14) is obtained in the form of slightly yellowish crystals, M.P. 150° C.

EXAMPLE 12

9.5 g (0.05 mole) of 2,2,6,6-tetramethyl-1-aza-4-thiacyclohexane-4,4-dioxide and 12.5 g (0.05 mole) of 3,5-ditert.butyl-4-hydroxybenzoic acid are stirred in 60 ml of ethanol for 2 hours at 60° C. After cooling, the salt that has crystallised out is filtered off under suction and recrystallised from ligroin. The resulting 3,5-ditert.-butyl-4-hydroxybenzoate of 2,2,6,6-tetramethyl-1-aza-4-thiacyclohexane-4,4-dioxide (15) melts at 132° C.

The corresponding salts are obtained in a similar manner when 2,2,6,6-tetramethyl-1-aza-4-thiacyclohexane-4,4-dioxide is reacted with acetic acid (16), lauric acid (17), stearic acid (18), oleic acid (19), benzoic acid (20), β-(3,5-ditert.-butyl-4-hydroxyphenyl)-propionic acid (21) or 3,5-ditert.-butyl-4-hydroxybenzylphosphonic acid monoethyl ester (22).

EXAMPLE 13

100 parts of polypropylene powder (Moplen Fibre grade of the firm Montedison) with 0.2 parts of β-(3,5-ditert.-butyl-4-hydroxyphenyl)-propionic acid octadecyl ester and 0.25 part of an agent protecting against light rays from the following Table I are homogenised in a Brabender plastograph at 200° C for 10 minutes. The mixture obtained is removed as quickly as possible from the kneader, and moulded in a toggle press into the form of a 2-3 mm thick sheet. A portion of the resulting moulded sheet is cut out and then pressed out between two highly polished hard aluminium sheets under a hand-hydraulic laboratory press for 6 minutes at 260° C, and with a pressure of 12 tons, to give a sheet 0.5 mm in thickness, which is immediately quenched in cold water. From this 0.5 mm sheet is then prepared, under constant conditions, the 0.1 mm thick test sheet material. Specimens each 60 × 44 mm in size are stamped out from this material and irradiated in the Xenotest 150. Specimens are removed at regular intervals of time from the exposure apparatus and their carbonyl content measured in an IR-spectrophotometer. The increase of the carbonyl extinction on exposure to light is a measure for the photooxidative decomposition of the polymer [cp. L. Balabán et al., J. Polymer Sci. Part C, 22, 1059–1071 (1969); J. F. Heacock, J. Polymer Sci. Part A-1, 22, 2921–34 (1969); D. J. Carlson and DM. Wiles, Macromolecules 2, 587–606 (1969)] and, as known from experience, is associated with a decline of the mechanical properties of the polymer. Thus, for example, the sheet stabilised only with antioxydans is completely brittle with the attainment of a carbonyl extinction of ca. 0.300. The protective action of the light protection agents according to the invention is clearly shown by the following Table I.

Table I

| Substance No. | Irradiation time hrs Xenotest 150 | Co-Extinction (5,85μ) |
|---|---|---|
| No agent protecting against light rays | 1000 | 0,300 |
| 1 | 5000 | < 0,010 |
| 2 | 5000 | < 0,010 |
| 3 | 4000 | < 0,010 |
| 4 | 4000 | < 0,010 |
| 5 | 4000 | < 0,010 |

EXAMPLE 14

1000 parts of polypropylene powder (melting index 1.5 g/10 minutes (230° C, 2160 g)) are mixed, in a drum mixer, with 1 part of β-(3,5-ditert.-butyl-4-hydroxyphenyl)propionic acid octadecyl ester and 5 parts of a compound from the following Table II, and the mixture is subsequented granulated in a Buss-Kokneter (kneader) at a temperature of 200° C.

The granulate thus obtained is processed, in the usual manner, through an extruder with a slot die into the form of a sheet; this is cut into strips that are subsequently stretched at elevated temperature with a stretch ratio of 1:6, and then wound up (Denier of strips: 700–900 den; tensile strength: 5.5–6.5 g/den).

The polypropylene strips prepared in the above manner are mounted without tension on specimen carriers and irradiated in a Xenotest apparatus 150. Five specimens are removed in each case after various intervals of time, and their tensile strength determined. The factor serving as a measure for the protective action of the individual agents protecting against light rays is the exposure time after which the tensile strength of the strips has decreased to 50% of the initial value. The values obtained are listed in the following table:

Table II

| Agent protecting against light rays | Hours exposure to reduce tensile strength 50% |
|---|---|
| none | 400 |
| Compound No. (1) | 2500 |
| Compound No. (2) | 2800 |
| Compound No. (3) | 2800 |
| Compound No. (4) | 3000 |
| Compound No. (5) | 3000 |
| Compound No. (6) | 2500 |

EXAMPLE 15

100 parts of polystyrene granules are mixed dry with 0.25 parts of an agent protecting against light rays from the following Table III; the mixture is re-granulated in an extruder, and subsequently processed with an injection-moulding machine into the form of sheets of 2 mm thickness. The sheets thus obtained are irradiated for 2000 hours in a Xenotest apparatus 150, and their yellowing values determined by means of the yellowing factor in the following manner:

$$\text{yellowing factor } (Y.F.) = \frac{\Delta T(420) - \Delta T(680)}{T(560)} \times 100$$

wherein $\Delta T$ denotes the transmission loss with the wave lengths 420 and 680 nm during exposure of the specimens and $T(560)$ is the transmission value as a percentage of the value in the case of the unexposed specimen at 560 nm. The results are given in Table III:

Table III

| Substance No. | Y.F. |
|---|---|
| No agent protecting against light rays | 20,0 |
| 1 | 4,5 |
| 2 | 5,5 |
| 3 | 4,0 |
| 11 | 5,5 |

EXAMPLE 16

A photographic colouring material made up of several layers and containing colour-forming couplers and agents protecting against light rays of formula I is prepared as follows: The following layers are applied successively to a triacetylcellulose film:

1. a layer consisting of a red-sensitive silver chloride bromide gelatine emulsion which contains a coupler (such as is described in the U.S. Pat. No. 2,423,730) that forms a blue-green dyestuff, and per liter of emulsion 3 g of an agent protecting against light rays from Table IV;
2. a gelatine interlayer;
3. a layer consisting of a green-sensitive silver chloride bromide gelatine emulsion containing a pyrazolone (Magenta-dyestuff-forming) coupler (such as is described in the U.S. Pat. No. 2,369,489) and, per liter of emulsion, 3 g of an agent protecting against light rays from Table IV;
4. a gelatine interlayer;
5. a layer consisting of a blue-sensitive silver iodide bromide gelatine emulsion containing a coupler forming a yellow dyestuff (such as is described in the U.S. Pat. Nos. 2,298,443 and 2,875,057) and, per liter of emulsion, 3 g of an agent protecting against light rays from Table IV;
6. a gelatine protective layer.

The coupler and agent protecting against light rays are used as dibutylphthalate solutions.

The colour film thus obtained is irradiated by a blue, a green and a red stepped photometric absorption wedge. The film is afterwards developed with a developer of the following composition:

2 g of 4-amino-N,N-diethyl-3-methylaniline hydrochloride,
20 g of sodium carbonate,
2 g of sodium sulphite (dewatered),
2 g of potassium bromide, made up with water to 1 liter.

After development, the film is washed with water, fixed, washed with water, bleached, washed again with water and dried.

The film is now exposed for 50 hours to a xenon lamp.

The reduction in colour intensity of this film is then compared with that of a film which has been prepared and exposed in exactly the same manner, but which had no agent protecting against light rays incorporated in it. For this comparison, the optical density is measured at three points which gave before exposure values of optical density of 0.5, 1.0 and 1.5. The reduction in colour intensity is calculated by dividing the difference between the optical density values before and after exposure to light by the density before exposure.

The measured decrease of colour intensity in % is given in the following Table IV:

Table IV

| | Optical density before exposure (irradiation) | 0,5 | 1,0 | 1,5 |
|---|---|---|---|---|
| colour film without agent protecting against light rays | blue-green | 22% | 19% | 19% |
| | magenta | 8% | 7% | 6% |
| | yellow | 52% | 40% | 36% |
| colour film with Compound (1) | blue-green | 5% | 5% | 4% |
| | magenta | 3% | 2% | 2% |
| | yellow | 17% | 16% | 18% |
| colour film with Compound (2) | blue-green | 6% | 4% | 4% |
| | magenta | 3% | 3% | 2% |
| | yellow | 17% | 16% | 16% |
| colour film with Compound (4) | blue-green | 6% | 5% | 4% |
| | magenta | 4% | 3% | 3% |
| | yellow | 18% | 17% | 16% |
| colour film with Compound (6) | blue-green | 4% | 5% | 4% |
| | magenta | 3% | 3% | 2% |
| | yellow | 18% | 18% | 16% |
| colour film with Compound (7) | blue-green | 5% | 5% | 4% |
| | magenta | 4% | 3% | 2% |
| | yellow | 17% | 16% | 16% |

From this evidence it is clear that the fastness to light of the colour pictures is appreciably increased by the addition of an agent protecting against light rays according to the invention.

EXAMPLE 17

1000 Parts of ABS granulate (Dow 500) containing 2 parts of 2,6-ditert.butyl-p-cresol and 2 parts of tris-nonylphenylphosphite, as primary stabilisation, are mixed in a drum mixer with 10 parts, or 5+5 parts for the synergistic mixtures, of the agents protecting against light rays from the following Table V, and subsequently extruded in an extruder at a maximum temperature of 220° C to give a granulate.

The resulting granulate is moulded in an automatic injection moulding machine into the form of a sheet 2-3 mm in thickness. A portion of the moulded sheet is cut out and pressed out between two highly polished hard aluminium sheets under a hand-hydraulic laboratory press for 6 minutes at 180° C, with a pressure of 40 tons, to form a 0.130 mm thick sheet, which is immediately quenched in cold water. Sections 60 × 44 mm in size are stamped out from this sheet and irradiated in an Atlas-Weather-o-meter. These specimens are removed from the exposure apparatus at regular intervals of time, and tested in an IR-spectrophotometer with respect to their carbonyl content. The increase of the carbonyl extinction on exposure is a measure for the photooxidative decomposition of the polymer [J. Shimada and K. Kabuki, J.A.P.S. 12, 655–669 and 671–682 (1968)] and, as shown by experience, is associated with a decrease of the mechanical properties of the polymer.

In the following Table V are listed the exposure times after which a carbonyl extinction (5.85 μ) of 0.300 has been attained. Clearly shown from these times is the synergistic action of the mixtures of agents protecting against light rays according to the invention. The light protecting agents designated by a substance-No. in the said Table V correspond to compounds contained in the stabiliser system that are given as examples in the general description.

Table V

| Substance No. | Hours of exposure in the Atlas-Weather-o-meter until a CO-Extinction of 0.300 is recorded |
|---|---|
| No agent protecting against light rays | 110 |
| 10 parts No. I. 2 | 250 |
| 10 parts No. I.22 | 230 |
| 10 parts No. I.20 | 200 |
| 10 parts No. II.2 | 350 |
| 10 parts No. III.1 | 300 |
| 10 parts No. IV.1 | 270 |
| 5 parts No. I. 2 +5 parts No. II.2 | >450 |
| 5 parts No. I. 2 +5 parts No. III.1 | >500 |
| 5 parts No. I. 2 +5 parts No. IV.1 | >500 |
| 5 parts No. I.22 +5 parts No. II.2 | >500 |
| 5 parts No. I.22 +5 parts No. III.1 | >500 |
| 5 parts No. I.22 +5 parts No. IV.1 | >500 |
| 5 parts No. I.20 +5 parts No. II.2 | >500 |
| 5 parts No. I.20 +5 parts No. III.1 | >500 |
| 5 parts No. I.20 +5 parts No. IV.1 | >500 |

EXAMPLE 18

1000 Parts of ABS-granulate (Dow 500) containing 2 parts of 2,6-ditert.butyl-p-eresol and 2 parts of trisnonylphenylphosphite as primary stabilisation are mixed in a drum mixer with 10 part, or 5 + 5 parts for the synergistic mixtures, of the agents protecting against light rays (light protecting agents) listed in the following Table VI, and subsequently extruded in an extruder at a maximum temperature of 220° C into the form of a granulate. This granulate is moulded in an automatic injection moulding machine to produce rods 2 mm thick, 6.8 mm wide and 60 mm long. These specimens are exposed in an Atlas-Weather-o-meter. The specimens are removed from the exposure apparatus at regular intervals of time, and their impact strength is then measured by means of an impact pendulum. The following Table VI contains the values obtained and shows the clear synergistic action of the claimed combinations.

The light protecting agents designated by a substance-No. in the following Table VI correspond to the compounds contained in the stabiliser system that are mentioned by way of example in the general description. The substances Nos. 1,2, I,20 and I.22 are identical to the light protecting agents denoted in the previous examples as compounds (1), (13) and (4).

Table VI

| Substance No. | Hours of exposure in the Atlas-Weather-o-meter until the impact strength recorded is: $10 \frac{Ep\ cm}{cm^2}$ |
|---|---|
| No agent protecting against light rays | 95 |
| 10 parts No. I. 2 | 250 |
| 10 parts No. I.22 | 220 |
| 10 parts No. I.20 | 230 |
| 10 parts No. II.2 | 160 |
| 10 parts No. III.1 | 180 |
| 10 parts No. IV.1 | 160 |
| 5 parts No. I.2 +5 parts No. II.2 | 380 |
| 5 parts No. I.2 +5 parts No. III.1 | 360 |
| 5 parts No. I.2 +5 parts No. IV.1 | 320 |
| 5 parts No. I.22 +5 parts No. II.2 | 350 |
| 5 parts No. I.22 +5 parts No. III.1 | 380 |
| 5 parts No. I.22 +5 parts No. IV.1 | 330 |
| 5 parts No. I.20 +5 parts No. II.2 | 370 |
| 5 parts No. I.20 +5 parts No. III.1 | 380 |
| 5 parts No. I.20 +5 parts No. IV.1 | 320 |

I claim:

1. A compound of formula I

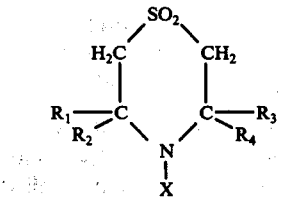

wherein $R_1$, $R_2$, $R_3$, and $R_4$ each independently are lower alkyl, $R_1$ and $R_2$ independently together with the carbon atom to which they are bound form a cycloalkyl ring, $R_3$ and $R_4$ independently together with the carbon atom to which they are bound form a cycloalkyl ring, or $R_1$ and $R_2$ and $R_3$ and $R_4$ together with the carbon atom to which they are bound form a cycloalkyl ring, and X is hydrogen; unsubstituted alkyl having 1 to 18 carbon atoms; alkyl having 2 to 20 carbon atoms which is substituted with hydroxy, carboxy, nitrile, sulphoxide, sulphone, or halo groups; —$CH_2COOR_8$ where $R_8$ is alkyl of 1 to 18 carbon atoms; —$R_9OOCR_{10}$ where $R_9$ is alkylene of 2 or 3 carbon atoms and $R_{10}$ is alkyl of 1 to 17 carbon atoms;

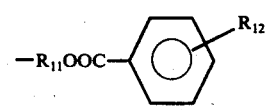

where $R_{11}$ is alkylene of 2 or 3 carbon atoms and $R_{12}$ is alkyl of 1 to 4 carbon atoms;

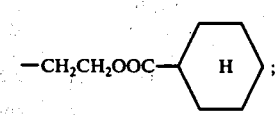

-continued

—CH₂CH₂OOCCH₂—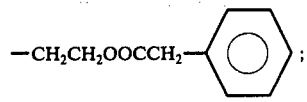;

—R₁₃NHCOR₁₄ where R₁₃ is alkylene of 2 or 3 carbon atoms and R₁₄ is alkyl of 1 to 17 carbon atoms; —R₁₅OR₁₆ where R₁₅ is alkylene or 2 carbon atoms and R₁₆ is alkyl of 1 to 8 carbon atoms; —R₁₇SR₁₈ where R₁₇ is alkylene of 2 or 3 carbon atoms and R₁₈ is alkyl of 1 to 8 carbon atoms or phenyl; R₁₉N(R₂₀)₂ where R₁₉ is alkylene of 2 or 3 carbon atoms and R₂₀ is independently H or alkyl of 1 or 2 carbon atoms; and —CH₂CH₂NHCH₂CH₂CN; alkenyl having 3 to 18 carbon atoms; alkynyl having 3 to 14 carbon atoms; benzyl, α-phenylethyl, α,α-dimethyl-benzyl, or such aralkyl groups substituted on the alkylene moiety by hydroxy, ester groups or halogen; acyl of the formula R₇CO— wherein R₇ is alkyl having 1 to 18 carbon atoms; the acyl radical derived from benzoic acid, p-tert. butylbenzoic acid, p-tert. octylbenzoic acid, methanesulfonic acid, benzenesulphonic acid or p-toluenesulfonic acid; halogen; —O; —NO; or NR₅R₆ wherein R₅ and R₆ each independently represent hydrogen; unsubstituted alkyl having 1 to 12 carbon atoms; alkyl having 2 to 12 carbon atoms which is substituted with hydroxy, carboxy, nitrile, sulphoxide, sulphone or halo groups; or R₅ is R₇CO— wherein R₇ is alkyl having 1 to 18 carbon atoms; or the acyl radical derived from benzoic acid, p-tert. butylbenzoic acid, p-tert. octylbenzoic acid, methanesulfonic acid, benzenesulphonic acid or p-toluenesulfonic acid; or R₅ and R₆ together with the nitrogen atom to which they are bound form the piperidine or morpholine ring, or its salts with organic or inorganic acids.

2. The compound of claim 1 wherein R₁, R₂, R₃ and R₄ are as defined in claim 1, and X is hydrogen; unsubstituted alkyl having 1 to 18 carbon atoms; alkyl having 2 to 20 carbon atoms which is substituted with hydroxy, carboxy, nitrile, sulphoxide, sulphone, or halo groups; —CH₂COOR₈ where R₈ is alkyl of 1 to 18 carbon atoms; —R₉OOCR₁₀ where R₉ is alkylene of 2 or 3 carbon atoms and R₁₀ is alkyl of 1 to 17 carbon atoms;

—R₁₁OOC—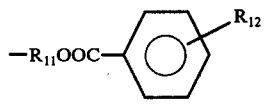

where R₁₁ is alkylene of 2 or 3 carbon atoms and R₁₂ is alkyl of 1 to 4 carbon atoms;

—CH₂CH₂OOC—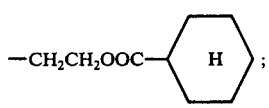;

—CH₂CH₂OOCCH₂—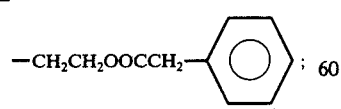;

—R₁₃NHCOR₁₄ where R₁₃ is alkylene of 2 or 3 carbon atoms and R₁₄ is alkyl of 1 to 17 carbon atoms; —R₁₅OR₁₆ where R₁₅ is alkylene or 2 carbon atoms and R₁₆ is alkyl of 1 to 8 carbon atoms; —R₁₇SR₁₈ where R₁₇ is alkylene of 2 or 3 carbon atoms and R₁₈ is alkyl of 1 to 8 carbon atoms or phenyl; R₁₉N(R₂₀)₂ where R₁₉ is alkylene of 2 or 3 carbon atoms and R₂₀ is independently H or alkyl of 1 or 2 carbon atoms; and —CH₂CH₂NHCH₂CH₂CN; alkenyl having 3 to 18 carbon atoms; alkynyl having 3 to 14 carbon atoms; benzyl, α-phenylethyl, α,α-dimethyl-benzyl, or such aralkyl groups substituted on the alkylene moiety by hydroxy, ester groups or halogen; acyl of the formula R₇CO— wherein R₇ is alkyl having 1 to 18 carbon atoms; the acyl radical derived from benzoic acid, p-tert. butylbenzoic acid, p-tert. octylbenzoic acid, methanesulfonic acid, benzenesulphonic acid or p-toluenesulfonic acid; halogen; —O.; —NO; or NR₅R₆ wherein R₅ and R₆ are defined as in claim 1, or its salts with organic or inorganic acids.

3. The compound according to claim 2, corresponding to the formula

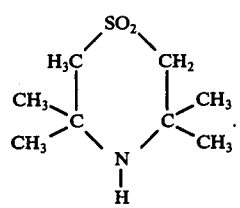

4. The compound according to claim 2, corresponding to the formula

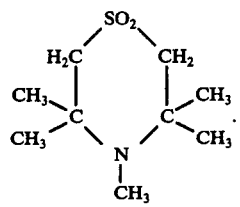

5. The compound according to claim 2, corresponding to the formula

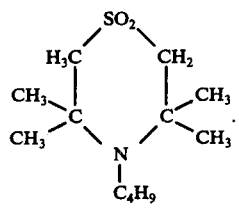

6. The compound according to claim 2, corresponding to the formula

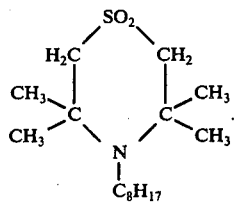

7. The compound according to claim 2, corresponding to the formula

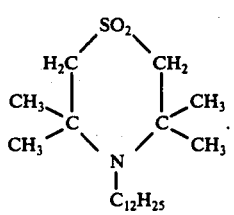

8. The compound of claim 1 wherein $R_1$, $R_2$, $R_3$ and $R_4$ are alkyl having 1 to 4 carbon atoms, or $R_1$ and $R_2$ and $R_3$ and $R_4$ together with the carbon atom to which they are bound form a cyclopentane or cyclohexane ring, and X as defined in claim 1, or its salts with hydrohalic acids, sulphuric acid, carboxylic acid, sulphonic acid or phosphorus-containing acids.

9. The compound of claim 1 wherein $R_1$, $R_2$, $R_3$ and $R_4$ are alkyl having 1 to 4 carbon atoms, or $R_1$ and $R_3$ and $R_4$ together with the carbon atom to which they are bound form a cyclopentane or cyclohexane ring, and X is hydrogen; unsubstituted alkyl having 1 to 18 carbon atoms; alkyl having 2 to 20 carbon atoms which is substituted with hydroxy, carboxy, nitrile, sulphoxide, sulphone, or halo groups; —$CH_2COOR_8$ where $R_8$ is alkyl of 1 to 18 carbon atoms; —$R_9OOCR_{10}$ where $R_9$ is alkylene of 2 or 3 carbon atoms and $R_{10}$ is alkyl of 1 to 17 carbon atoms;

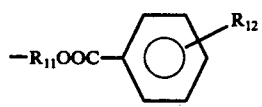

where $R_{11}$ is alkylene of 2 or 3 carbon atoms and $R_{12}$ is alkyl of 1 to 4 carbon atoms;

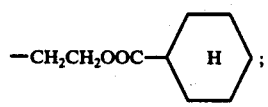

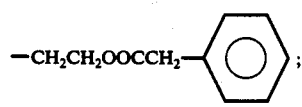

—$R_{13}NHCOR_{14}$ where $R_{13}$ is alkylene of 2 or 3 carbon atoms and $R_{14}$ is alkyl of 1 to 17 carbon atoms; —$R_{15}OR_{16}$ where $R_{15}$ is alkylene or 2 carbon atoms and $R_{16}$ is alkyl of 1 to 8 carbon atoms; —$R_{17}SR_{18}$ where $R_{17}$ is alkylene of 2 or 3 carbon atoms and $R_{18}$ is alkyl of 1 to 8 carbon atoms or phenyl; $R_{19}N(R_{20})_2$ where $R_{19}$ is alkylene of 2 or 3 carbon atoms and $R_{20}$ is independently H or alkyl of 1 or 2 carbon atoms; and —$CH_2CH_2NHCH_2CH_2CN$; alkenyl having 3 to 18 carbon atoms; alkynyl having 3 to 14 carbon atoms; benzyl, α-phenylethyl, α,α-dimethyl-benzyl, or such aralkyl groups substituted on the alkylene moiety by hydroxy, ester groups or halogen; acyl of the formula $R_7CO$— wherein $R_7$ is alkyl having 1 to 18 carbon atoms; the acyl radical derived from benzoic acid, p-tert. butylbenzoic acid, p-tert. octylbenzoic acid, methanesulfonic acid, benzenesulphonic acid or p-toluenesulfonic acid; halogen; —O. ; —NO; or $NR_5R_6$ wherein $R_5$ and $R_6$ are as defined as in 1, or its salts with hydrohalic acids, sulphuric acid, carboxylic acids, sulphonic acids or phosphorus-containing acids.

10. The compound of claim 1 wherein $R_1$, $R_2$, $R_3$ and $R_4$ are alky, having 1 or 2 carbon atoms, or $R_1$ and $R_2$ and $R_3$ and $R_4$ together with the carbon atom to which they are bound form a cyclohexane ring, and X is hydrogen; unsubstituted alkyl having 1 to 12 carbon atoms; alkyl having 2 to 20 carbon atoms which is substituted with hydroxy; carboxy; nitrile; sulphoxide or sulphone; $CH_2COOR_8$ where $R_8$ is alkyl of 1 to 18 carbon atoms; —$R_9OOCR_{10}$ where $R_9$ is alkylene of 2 or 3 carbon atoms and $R_{10}$ is alkyl of 1 to 17 carbon atoms;

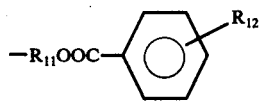

where $R_{11}$ is alkylene of 2 or 3 carbon atoms and $R_{12}$ is alkyl of 1 to 4 carbon atoms;

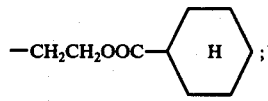

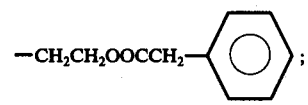

—$R_{13}NHCOR_{14}$ where $R_{13}$ is alkylene of 2 or 3 carbon atoms and $R_{14}$ is alkyl of 1 to 17 carbon atoms; —$R_{15}OR_{16}$ where $R_{15}$ is alkylene or 2 carbon atoms and $R_{16}$ is alkyl of 1 to 8 carbon atoms; —$R_{17}SR_{18}$ where $R_{17}$ is alkylene of 2 or 3 carbon atoms and $R_{18}$ is alkyl of 1 to 8 carbon atoms or phenyl; $R_{19}N(R_{20})_2$ where $R_{19}$ is alkylene of 2 or 3 carbon atoms and $R_{20}$ is independently H or alkyl of 1 or 2 carbon atoms; and —$CH_2CH_2NHCH_2CH_2CN$; alkenyl having 3 to 8 carbon atoms; propargyl; benzyl, α-phenylethyl, α,α-dimethylbenzyl, or such aralkyl groups substituted on the alkylene moiety by hydroxy, carboxylic acid ester groups, or halogen; acyl of the fromula $R_7CO$— wherein $R_7$ is alkyl having 1 to 12 carbon atoms; the acyl radical derived from benzoic acid, p-tert. butylbenzoic acid, p-tert. octylbenzoic acid, methanesulfonic acid, benzenesulfonic acid or p-toluenesulfonic acid; bromine; chlorine; —O.; or —$NR_5R_6$ wherein $R_5$ and $R_6$ each independently are hydrogen; alkyl having 1 to 4 carbon atoms; or $R_5$ is $R_7CO$— wherein $R_7$ is alkyl having 1 to 18 carbon atoms; or the acyl radical derived from benzoic acid, p-tert. butylbenzoic acid, p-tert. octylbenzoic acid, methanesulfonic acid, benzenesulphonic acid or p-toluenesulfonic acid; or its salts with hydrohalic acids, sulphuric acid, phosphoric acid, carboxylic acids having 1 to 18 carbon atoms, sulphonic acids having 1 to 12 carbon atoms or phosphorus- organic acids having 1 to 20 carbon atoms.

11. The compound of claim 1 wherein $R_1$, $R_2$, $R_3$, and $R_4$ are alkyl having 1 or 2 carbon atoms, or $R_1$ and $R_2$ and $R_3$ and $R_4$ together with the carbon atom to which they are bound form a cyclohexane ring, and X is hydrogen; unsubstituted alkyl having 1 to 12 carbon atoms; alkyl having 2 to 20 carbon atoms which is substituted with hydroxy; carboxy; nitrile; sulphoxide or sulphone; $CH_2COOR_8$ where $R_8$ is alkyl of 1 to 18 carbon atoms; —$R_9OOCR_{10}$ where $R_9$ is alkylene or 2 or 3 carbon atoms and $R_{10}$ is alkyl of 1 to 17 carbon atoms;

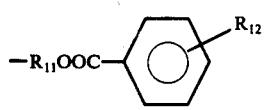

where $R_{11}$ is alkylene of 2 or 3 carbon atoms and $R_{12}$ is alkyl of 1 to 4 carbon atoms;

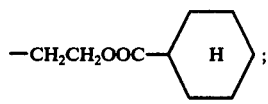

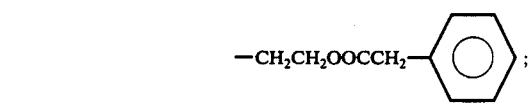

—$R_{13}NHCOR_{14}$ where $R_{13}$ is alkylene of 2 or 3 carbon atoms and $R_{14}$ is alkyl of 1 to 17 carbon atoms; —$R_{15}OR_{16}$ where $R_{15}$ is alkylene or 2 carbon atoms and $R_{16}$ is alkyl of 1 to 8 carbon atoms; —$R_{17}SR_{18}$ where $R_{17}$ is alkylene of 2 or 3 carbon atoms and $R_{18}$ is alkyl of 1 to 8 carbon atoms or phenyl; $R_{19}N(R_{20})_2$ where $R_{19}$ is alkylene of 2 or 3 carbon atoms and $R_{20}$ is independently H or alkyl of 1 or 2 carbon atoms; and —$CH_2CH_2NHCH_2CH_2CN$; alkenyl having 3 to 8 carbon atoms; propargyl; benzyl, α-phenylethyl, α,α-dimethylbenzyl, or such aralkyl groups substituted on the alkylene moiety by hydroxy, carboxylic acid ester groups, or halogen; acyl of the formula $R_7CO$— wherein $R_7$ is alkyl having 1 to 12 carbon atoms; the acyl radical derived from benzoic acid, p-tert. butylbenzoic acid, p-tert. octylbenzoic acid, methanesulfonic acid, benzenesulfonic acid or p-toluenesulfonic acid; bromine; chlorine; —O., or —$NR_5R_6$ wherein $R_5$ and $R_6$ each independently are hydrogen; alkyl having 1 to 4 carbon atoms; or $R_5$ is $R_7CO$— wherein $R_7$ is alkyl having 1 to 12 carbon atoms; the acyl radical derived from benzoic acid, p-tert. butylbenzoic acid, p-tert. octylbenzoic acid, methanesulfonic acid, benzenesulfonic acid or p-toluenesulfonic acid; or its salts with hydrohalic acids, sulphuric acid, phosphoric acid, carboxylic acids having 1 to 18 carbon atoms, sulphonic acids having 1 to 12 carbon atoms or phosphorus-organic acids having 1 to 20 carbon atoms.

12. The compound of claim 1 of formula Ia

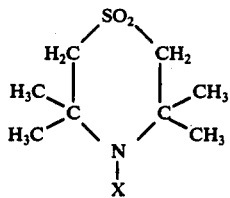

(Ia)

wherein X is hydrogen, alkyl having 1 to 12 carbon atoms, alkenyl having 3 to 4 carbon atoms, propargyl, benzyl α-phenylethyl, α,α-dimethylbenzyl, bromine, chlorine, —O., or —$NR_5R_6$ wherein $R_5$ and $R_6$ each independently are hydrogen, alkyl having 1 to 4 carbon atoms, or $R_5$ is alkyl- carbonyl having 2 to 12 carbon atoms, alkoxycarbonyl having 2 to 9 carbon atoms or benzoyl, or its salts with carboxylic acids having 1 to 18 carbon atoms or phosphorus-organic acids having 1 to 20 carbon atoms.

13. The compound of claim 1 of formula Ia

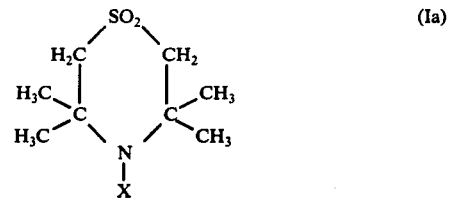

(Ia)

wherein X is hydrogen, alkyl having 1 to 12 carbon atoms, alkenyl having 3 to 4 carbon atoms, propargyl, benzyl, α-phenylethyl, α,α-dimethylbenzyl, —O., or —$NR_5R_6$ wherein $R_5$ and $R_6$ each independently are hydrogen, alkyl having 1 to 4 carbon atoms, or $R_5$ is alkylcarbonyl having 2 to 12 carbon atoms, alkoxycarbonyl having 2 to 9 carbon atoms, or benzoyl, or its salts with carboxylic acids having 1 to 18 carbon atoms, or with phosphorus-organic acids having 1 to 20 carbon atoms.

14. The compound of claim 1 of formula Ia

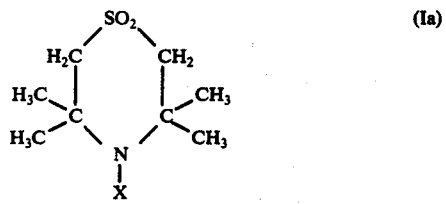

(Ia)

wherein X is hydrogen, alkyl having 1 to 12 carbon atoms, cyanomethyl, alkenyl having 3 carbon atoms, propargyl, chlorine, bromine, —O., —NO, or —$NR_5R_6$ wherein $R_5$ and $R_6$ are hydrogen, or $R_5$ is alkylcarbonyl having 2 to 12 carbon atoms, ethoxycarbonyl or benzoyl, or its salts with 3,5- di-tert.butyl-4-hydroxybenzoic acid.

15. The compound of claim 1 of formula Ia

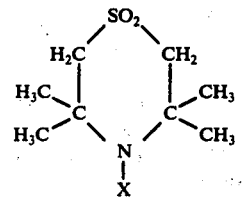

wherein X is hydrogen, alkyl having 1 to 12 carbon atoms, cyanomethyl, alkenyl having 3 carbon atoms, propargyl, —O., —NO or —$NR_5R_6$ wherein $R_5$ and $R_6$ are hydrogen, or $R_5$ is alkylcarbonyl having 2 to 12 carbon atoms, ethoxycarbonyl or benzoyl, or its salts with 3,5-di-tert.butyl-4-hydroxybenzoic acid.

* * * * *